(12) United States Patent
Boderke et al.

(10) Patent No.: US 8,394,857 B2
(45) Date of Patent: Mar. 12, 2013

(54) 1-AMINO-ALKYLCYCLOHEXANE DERIVATIVES FOR THE TREATMENT OF INFLAMMATORY SKIN DISEASES

(75) Inventors: Peter Boderke, Schwalbach (DE); Alexander Gebauer, Wiesbaden (DE); Bhushan Hardas, Summerfield, NC (US); Bernhard Hauptmeier, Gelnhausen (DE); Rainer Pooth, Bad Soden/Taunus (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 433 days.

(21) Appl. No.: 12/653,865

(22) Filed: Dec. 18, 2009

(65) Prior Publication Data

US 2010/0197792 A1   Aug. 5, 2010

Related U.S. Application Data

(60) Provisional application No. 61/203,195, filed on Dec. 19, 2008.

(30) Foreign Application Priority Data

Feb. 3, 2009   (EP) ..................................... 09001448

(51) Int. Cl.
  *A61K 31/13* (2006.01)
(52) U.S. Cl. ........................................................ 514/579
(58) Field of Classification Search .................... 514/579
  See application file for complete search history.

(56) References Cited

U.S. PATENT DOCUMENTS

| | | | |
|---|---|---|---|
| 6,057,364 A | 5/2000 | Jasys et al. | |
| 6,221,887 B1 | 4/2001 | Asghar et al. | |
| 6,616,933 B1 | 9/2003 | Breton et al. | |
| 7,851,501 B2 * | 12/2010 | Aydt et al. | ..................... 514/438 |
| 2002/0058010 A1 | 5/2002 | Picard-Lesboueryries et al. | |
| 2004/0102525 A1 | 5/2004 | Kozachuk | |
| 2005/0137122 A1 | 6/2005 | Sharif | |
| 2005/0196418 A1 | 9/2005 | Yu et al. | |
| 2007/0141148 A1 | 6/2007 | Hauptmeier et al. | |
| 2011/0251283 A1 | 10/2011 | Kurzen | |

FOREIGN PATENT DOCUMENTS

| | | |
|---|---|---|
| AU | 2004251636 | 1/2005 |
| EP | 0904777 | 3/1999 |
| EP | 1184031 | 10/2007 |
| EP | 1952797 | 8/2008 |
| WO | WO95/32945 | 12/1995 |
| WO | WO98/04537 | 2/1998 |
| WO | 01/98253 | 12/2001 |
| WO | WO2004/043899 | 5/2004 |
| WO | WO2005/009421 | 2/2005 |
| WO | 2005/044228 | 5/2005 |
| WO | WO2007/148113 | 6/2007 |
| WO | WO2007/082206 | 7/2007 |
| WO | WO2007/103687 | 9/2007 |

OTHER PUBLICATIONS

European Search Report for EP 09001448 of May 27, 2009.
Finch, et al., Pain, 2009.
Fuziwara, et al., J. Invest. Dermatol., 2003, 120. 1023-1029.
International Search Report for PCT/EP2009/009151 dated Mar. 19, 2010.
International Search Report for PCT/EP2009/009153 dated Mar. 19, 2010.
Kurzen, et al., Exp. Dermatol., 2004, 13 (Suppl. 4), 27-30.
Kurzen, et al., J. Invest. Dermatol., 2004, 123, 937-949.
Plazas, et al., Eur. J. Pharrnacol., 2007, 566, 11-19.
Rammes, et al., IDrugs, 2006, 9, 128-135.
Schwarz, et al., Journal of Immunology, 2004. 172, 1036-1043.

* cited by examiner

*Primary Examiner* — Rei-tsang Shiao
(74) *Attorney, Agent, or Firm* — Hueschen and Sage

(57) ABSTRACT

The present invention relates to the treatment of an individual afflicted with inflammatory skin diseases comprising administering to the individual an effective amount of a 1-aminoalkylcyclohexane derivative.

21 Claims, 5 Drawing Sheets

Fig. 1. Effect of neramexane mesylate on skin sensitization. Results are mean±SEM. *p<0.05 vs. positive control (Dunnett test)

Fig 2 Effect of neramexane mesylate on skin sensitization. Results are mean±SEM.

Fig. 3. Effect of neramexane mesylate on skin sensitization. Results are mean±SEM.
*p<0.05 vs. positive control (Dunnett test)

Fig. 4. Effect of neramexane mesylate on dermatitis response 7 and 24 hr after the challenge. Data are analysed using Student t-test. *- p<0.05 v.s. Croton oil alone. Results are expressed as mean±SEM.

Fig. 5. Effect of neramexane mesylate on dermatitis response 7 and 24 hr after the challenge. Data are analysed by Student t-test (Croton oil vs. Neramexane+Croton Oil). Results are expressed as mean±SEM.

1-AMINO-ALKYLCYCLOHEXANE DERIVATIVES FOR THE TREATMENT OF INFLAMMATORY SKIN DISEASES

FIELD OF THE INVENTION

The present invention relates to the treatment of an individual afflicted with inflammatory skin diseases, comprising administering to the individual an effective amount of a 1-amino-alkylcyclohexane derivative.

BACKGROUND OF THE INVENTION

This invention relates to methods of treating patients afflicted with inflammatory skin diseases, including acne, rosacea, eczema, atopic dermatitis, psoriasis and oily skin.

Acne is the most common skin disease. Epidemiologic data suggest that up to 80% of individuals may be affected. Men and women develop acne about equally, and the onset of the disease typically occurs at age 10-14 years and regresses by age 20-25 years. In some patients acne persists into fourth or fifth decade of life (persistent acne). The clinical spectrum of acne ranges from mild manifestations (e.g., a few comedones (acne lesions) with occasional inflamed papulopustules to "clinical" acne in more severe cases) to severe inflammation and abscess formation on the face or upper trunk. Follicular rupture may follow leading to a foreign body reaction including abscesses, fistulas and systemic signs of inflammation (acne conglobata).

Increased sebum production, which is believed to be regulated by androgens is thought to be one of the main causes of acne (seborrhea) development. A further prerequisite for developing acne is a disturbed follicular keratinisation leading to hyperkeratosis. Factors responsible for follicular hyperkeratosis include the following: localized, follicular linolic acid deficiency, comedogenic sebum components, changes in the lipid composition of sebum, bacterial metabolites and mediators of inflammation.

Propionibacteria (*Propionibacterium acnes*) are the dominant bacteria in hair follicles. These bacteria prefer microaerobic or anaerobic conditions and preferentially colonize regions with high sebum production. A four log higher concentration of propionibacteria is found in 11-20 year olds with acne compared to 11-20 year olds without acne. Bacterial lipases release irritative and pro-inflammatory free acids and other potentially pro-inflammatory bacterial metabolites such as proteases, hyaluronidases and chemotactic factors. Metabolites of propionibacteria induce follicular and perifollicular inflammation, especially due to chemotactic substances. Other immunological and inflammatory factors play also a role in the development and course of acne (e.g., toll-like receptor 2, IL-1, IL-8, LTB4, PPAR alpha).

There are a number of topical as well as systemic treatment options available for acne. Topical treatments for acne include: Retinoids, which normalise follicular keratinisation; Benzoylperoxide (BPO), which is an anti-bacterial agent that reduces *Propionibacterium acnes* (*P. acnes*) within the follicle; and topical antibiotics with an antibacterial effect. Systemic treatment options for acne include antibiotics. Systemic treatment options also include hormones for female patients.

Rosacea is a common, chronic cutaneous inflammatory disease, primarily of the facial skin. It is common in the third and fourth decade of life, peaking at the age of 40 and 50 years. The causes of rosacea have not yet been identified. Facial vascular reactivity, dermal connective tissue structure or composition, pilosebeaceous structure, microbial colonization and a combination of factors that alter the cutaneous response to rosacea trigger factors, respectively, are seen as major pathogenic mechanisms. Important trigger factors among others appear to be hot or cold temperature, sunlight, wind, hot drinks, spicy food, alcohol, exercise, emotions, and topical irritants which lead to flushing and blushing. Early stage rosacea is characterized by persistent erythema and teleangiectasia, predominantly of the cheeks, frequently followed by papules and papulopustules. In later stages, diffuse hyperplasia of connective tissue and sebaceous glands may occur. This can cause a hypertrophy of the nose, a so-called rhinophyma. Rosacea occurs in stages and may affect the eyes, most commonly resulting in blepharitis and conjunctivitis. Rosacea may occur in areas other than the face, such as retroauricular areas, as well as on the neck, chest, back and scalp. The clinical appearance of rosacea may be similar to acne, but, in contrast, rosacea is not a primary follicular disease.

Oral tetracycline antibiotics, such as tetracycline, doxycycline, and minocycline, and topical antibiotics, such as metronidazole, which are used in acne, are also a treatment option for rosacea and are used to relieve papules, pustules, inflammation and some redness.

Eczema is a general term encompassing various inflamed skin conditions such as atopic dermatitis, allergic contact dermatitis and occupational dermatitis.

Atopic dermatitis is a pruritic that typically starts in early infancy (although an adult-onset variant is recognized). Atopic dermatitis is characterized by pruritus, eczematous lesions, xerosis (dry skin), and lichenification (thickening of the skin and an increase in skin markings).

Atopic dermatitis results from complex interactions between genetic susceptibility genes resulting in a defective skin barrier, defects in the innate immune system, and heightened immunological responses to allergens and microbial antigens. The dysfunction of the barrier is caused by down-regulation of cornified envelope genes (fillagrin and loricrin), reduced ceramide levels, increased levels of endogenous proteolytic enzymes, and enhanced transepidermal water loss. Disturbance of the barrier may also be caused by soaps and detergents and/or by exposure to exogenous proteases from house dust mites and *Staphylococcus aureus*. This is worsened by the lack of certain endogeneous protease inhibitors in atopic skin. These epidermal changes likely contribute to increased allergen absorption into the skin and microbial colonization. Current thinking is that microbial superantigens play a major role; they can more easily penetrate into the viable skin layers via the disturbed barrier and induce an influx of T cells (predominantly activated memory T cells suggesting previous encounter with antigen) with occasional macrophages.

Pruritus is a prominent feature of atopic dermatitis, manifested as cutaneous hyperreactivity and scratching following exposure to allergens, changes in humidity, sweating, and low concentrations of irritants. The mechanisms of pruritus are poorly understood; however, it is believed that inflammatory cells play an important role. There is an itch-scratch cycle. Repetitive scratching activates areas in the prefrontal cortex and orbifrontal cortex. This may explain the hedonic and compulsive components of scratching and may be associated with release of endogenous opioids. Repetitive scratching in atopic dermatitis causes secretion of neuropeptides and opiates that may further augment the vicious itch-scratch cycle.

Psoriasis is a polygenetic hereditary multifactor inflammatory skin disease of unknown pathogenesis, which may be influenced by a number of environmental factors. There is a strong genetic basis leading to complex alterations in epidermal growth and differentiation and multiple biochemical, immunological, and vascular abnormalities, and a poorly understood relationship to nervous system function. The pathogenesis of psoriasis is rather complex involving local and systemic factors. At present, the abnormal epidermal hyperproliferation is regarded as a secondary phenomenon following T-lymphocyte mediated autoimmune reaction. It has also been reported that immunological reaction to *Streptococcus* species may also play a role. Epidermal proliferation in lesional skin is characterized by increased recruitment of cycling cells from the resting G0 population. In contrast to older data, cell cycle times in the psoriatic lesion are essentially normal. In particular, the suprabasal compartment is characterized by expression of molecules that are absent or have restricted expression in normal skin. In primary keratinocyte cultures, soluble factors from CD4+ T-lymphocyte clones derived from psoriatic plaques promote proliferation of the psoriatic CD29+ keratin-10 subpopulation, whereas CD29+ keratin-10 keratinocytes from normal subjects failed to have such a growth response to soluble factors from the same T cell clones. This suggests that a subpopulation of epidermal cells derived from psoriatic plaques do respond abnormally to T-lymphocyte clones from psoriatic plaques.

Oily skin is due to excessive sebum production by sebaceous glands. Excessive sebum production may be caused by hormonal imbalances during pregnancy and menopause, heredity, diet, birth control pills, cosmetics use or humidity and hot weather or diseases such as Morbus Parkinson.

Excess sebum produces surface oiliness, blocks pores, provides nourishment to bacteria that live upon the skin (*P. acnes*) and contributes to acne flare-ups.

Impetigo contagiosa is a superficial bacterial skin infection most common among school children. People who play close contact sports such as rugby and wrestling are also susceptible, regardless of age. Impetigo is not as common in adults. It is highly contagious and also known as school sores. It is primarily caused by *Staphylococcus aureus* and by *Streptococcus pyogenes*. Impetigo generally appears as honey-colored scabs formed from dried serum, and is often found on the arms, legs, or face. The infection is spread by direct contact with lesions or with nasal carriers. The incubation period is 1-3 days. Dried streptococci in the air are not infectious to intact skin. Scratching may spread the lesions. Good hygiene practices can help prevent impetigo from spreading.

Subtypes of impetigo contagiosa are bullous impetigo and ecthyma. Bullous impetigo primarily affects infants and children younger than 2 years. It causes painless, fluid-filled blisters—usually on the trunk, arms and legs. The skin around the blister is usually red and itchy but not sore. The blisters, which break and scab over with a yellow-colored crust, may be large or small, and may last longer than sores from other types of impetigo. Ecthyma is a more serious form of impetigo in which the infection penetrates deeper into the skin's second layer, the dermis. Signs and symptoms include:
  Painful fluid- or pus-filled sores that turn into deep ulcers, usually on the legs and feet
  A hard, thick, gray-yellow crust covering the sores
  Swollen lymph glands in the affected area
  Little holes the size of pinheads to the size of pennies appear after crust recedes
  Scars that remain after the ulcers heal For the treatment of impetigo contagiosa and its subtypes topical or oral antibiotics are usually prescribed. Mild cases can be treated with bactericidal ointment, such as fusidic acid, mupirocin, chloramphenicol, clioquinol or neosporin. More severe cases require oral antibiotics, such as dicloxacillin, flucloxacillin or erythromycin. Alternatively amoxicillin combined with clavulanate potassium, cephalosporins (1st generation) and many others may also be used as an antibiotic treatment. The mentioned medicaments may be used in the form of any of pharmaceutically acceptable salts, optical isomers, diastereomers, enantiomers, hydrates, and pharmaceutically acceptable salts thereof.

There are various disadvantages associated with the available treatments for inflammatory skin diseases.

Retinoids are an available treatment options for acne. Clinical improvement following treatment with Retinoids typically requires several weeks, and Retinoids are known to possess teratogenic properties. Retinoids may also be irritants. Onset of action is quite rapid with BPO and resistance to *P. Acnes* has not been reported; however, BPO is a bleaching agent and, therefore, whitening of clothing and bedding may occur. Furthermore, BPO is a potential irritant and may act as a mutagen. The number of topical antibiotics currently used has led to high percentage of resistance. Thus, a need exists for improved treatments for acne and other inflammatory skin diseases.

1-Amino-alkylcyclohexane derivatives such as neramexane (also known as 1-amino-1,3,3,5,5-pentamethylcyclohexane) have been found to be useful in the therapy of various diseases especially in certain neurological diseases, including Alzheimer's disease and neuropathic pain. 1-Amino-alkylcyclohexane derivatives such as neramexane are disclosed in detail in U.S. Pat. Nos. 6,034,134 and 6,071,966, the subject matter of which patents is hereby incorporated by reference.

Surprisingly, it has now been found that 1-amino-alkylcyclohexane derivatives such as neramexane are also suitable for treating inflammatory skin diseases.

The beneficial impact of 1-amino-alkylcyclohexane derivatives such as neramexane on sebocytes also contributes to the effective treatment of inflammatory skin diseases including acne, rosacea, eczema, atopic dermatitis, psoriasis and oily skin. The impact on proliferation and/or differentiation of sebocytes and thus the ability to reduce lipid production allows for regulation of sebum secretion. In addition to overall sebum regulation, the composition of sebum may also be influenced, leading to normalization of the pathophysiological phenotype of the diseased hair-follicle.

Patients with inflammatory skin diseases often exhibit a disturbed cutaneous barrier function. 1-Amino-alkylcyclohexane derivatives such as neramexane may improve the cutaneous barrier function and block the delay of barrier recovery which results in a positive effect on homeostasis of the skin.

SUMMARY OF THE INVENTION

The present invention relates to a method of treating inflammatory skin diseases such as acne, rosacea, eczema, atopic dermatitis, psoriasis and oily skin in a subject in need thereof, comprising administering to the individual an effective amount of a 1-amino-alkylcyclohexane derivative (e.g., neramexane or a pharmaceutically acceptable salt thereof such as neramexane mesylate).

The present invention also relates to a method of treating an inflammatory skin disease such as impetigo contagiosa.

A further aspect of the invention relates to such a method wherein neramexane mesylate is administered in a range from about 5 mg to about 150 mg/day or neramexane mesylate is administered in a range from about 5 mg to about 100 mg/day, or neramexane mesylate is administered in a range from about 5 mg to about 75 mg/day, or wherein neramexane mesylate is administered at about 50 mg/day or wherein neramexane mesylate is administered at about 75 mg/day for example in an oral formulation.

A further aspect of the invention relates to such a method wherein the 1-amino-alkylcyclohexane derivative (e.g., neramexane or a pharmaceutically acceptable salt thereof such as neramexane mesylate) is administered once a day, twice a day (b.i.d.), or three times a day.

A further aspect of the invention relates to such a method wherein the 1-amino-alkylcyclohexane derivative (e.g., neramexane or a pharmaceutically acceptable salt thereof such as neramexane mesylate) is administered in an immediate release formulation.

A further aspect of the invention relates to such a method wherein the 1-amino-alkylcyclohexane derivative (e.g., neramexane or a pharmaceutically acceptable salt thereof such as neramexane mesylate) is administered in a modified release formulation.

A further aspect of the invention relates to such a method wherein the 1-amino-alkylcyclohexane derivative (e.g., neramexane or a pharmaceutically acceptable salt thereof such as neramexane mesylate) is administered in a topical formulation such as a topical rinse-off or leave-on formulation.

A further aspect of the invention relates to such a method wherein the 1-amino-alkylcyclohexane derivative (e.g., neramexane or a pharmaceutically acceptable salt thereof such as neramexane mesylate) is administered between 0.1 and 99% by weight of the formulation.

A further aspect of the invention relates to such a method wherein the 1-amino-alkylcyclohexane derivative (e.g., neramexane or a pharmaceutically acceptable salt thereof such as neramexane mesylate) is administered in an oral formulation.

A further aspect of the invention relates to such a method wherein the 1-amino-alkylcyclohexane derivative (e.g., neramexane or a pharmaceutically acceptable salt thereof such as neramexane mesylate) is administered systemically.

A further aspect of the invention relates to a method of treating inflammatory skin diseases in a subject in need thereof, comprising administering to the individual an effective amount of a 1-amino-alkylcyclohexane derivative (e.g., neramexane or a pharmaceutically acceptable salt thereof such as neramexane mesylate) and an additional pharmaceutical agent (e.g., antimicrobial agents, antibiotics, retinoids or steroids) which has been shown to be effective in treating or preventing inflammatory skin diseases.

A further aspect of the invention relates to a method of treating acne in a subject in need thereof, comprising administering to the individual an effective amount of a 1-amino-alkylcyclohexane derivative (e.g., neramexane or a pharmaceutically acceptable salt thereof such as neramexane mesylate) and an additional pharmaceutical agent (e.g., antimicrobial agents, antibiotics, retinoids or steroids) which has been shown to be effective in treating or preventing inflammatory skin diseases.

A further aspect of the invention relates to a method of treating acne in a subject in need thereof, comprising administering to the individual an effective amount of a 1-amino-alkylcyclohexane derivative (e.g., neramexane or a pharmaceutically acceptable salt thereof such as neramexane mesylate) and an additional pharmaceutical agent (e.g., antimicrobial agents, antibiotics, retinoids, steroids, or other non-specific agents) which has been shown to be effective in treating or preventing acne.

A further aspect of the invention relates to such a method wherein the 1-amino-alkylcyclohexane derivative (e.g., neramexane or a pharmaceutically acceptable salt thereof such as neramexane mesylate) and the additional pharmaceutical agent (e.g., antimicrobial agents, antibiotics, retinoids or steroids) are administered conjointly.

A further aspect of the invention relates to such a method wherein the 1-amino-alkylcyclohexane derivative (e.g., neramexane or a pharmaceutically acceptable salt thereof such as neramexane mesylate) and the additional pharmaceutical agent (e.g., antimicrobial agents, antibiotics, retinoids or steroids) are administered in a single formulation.

A further aspect of the invention relates to such a method wherein the 1-amino-alkylcyclohexane derivative (e.g., neramexane or a pharmaceutically acceptable salt thereof such as neramexane mesylate) and the additional pharmaceutical agent (e.g., antimicrobial agents, antibiotics, retinoids or steroids) are administered in a topical formulation such as a topical rinse-off or leave-on formulation.

A further aspect of the invention relates to such a method wherein the 1-amino-alkylcyclohexane derivative (e.g., neramexane or a pharmaceutically acceptable salt thereof such as neramexane mesylate) and the additional pharmaceutical agent (e.g., antimicrobial agents, antibiotics, retinoids or steroids) are administered systemically.

A further aspect of the invention relates to such a method wherein the 1-amino-alkylcyclohexane derivative (e.g., neramexane or a pharmaceutically acceptable salt thereof such as neramexane mesylate) and the additional pharmaceutical agent (e.g., antimicrobial agents, antibiotics, retinoids or steroids) are administered in an oral formulation.

A further aspect of the invention relates to a 1-amino-alkylcyclohexane derivative (e.g., neramexane or a pharmaceutically acceptable salt thereof such as neramexane mesylate) for the treatment of inflammatory skin diseases such as acne, rosacea eczema, atopic dermatitis, psoriasis, and oily skin.

A further aspect of the invention relates to a 1-amino-alkylcyclohexane derivative (e.g., neramexane or a pharmaceutically acceptable salt thereof such as neramexane mesylate) for the treatment of a inflammatory skin disease such as impetigo contagiosa.

A further aspect of the invention relates to the use of a 1-amino-alkylcyclohexane derivative (e.g., neramexane or a pharmaceutically acceptable salt thereof such as neramexane mesylate) for the manufacture of a medicament for treatment of inflammatory skin diseases.

A further aspect of the invention relates to the above-defined derivative or use wherein neramexane mesylate is administered in a range from about 5 mg to about 150 mg/day or neramexane mesylate is administered in a range from about 5 mg to about 100 mg/day, or neramexane mesylate is administered in a range from about 5 mg to about 75 mg/day, or wherein neramexane mesylate is administered at about 50 mg/day or wherein neramexane mesylate is administered at about 75 mg/day for example in an oral formulation.

A further aspect of the invention relates to the above-defined derivative or use wherein the 1-amino-alkylcyclohexane derivative (e.g., neramexane or a pharmaceutically acceptable salt thereof such as neramexane mesylate) is administered once a day, twice a day (b.i.d.), or three times a day.

A further aspect of the invention relates to the above-defined derivative or use wherein the 1-amino-alkylcyclohexane derivative (e.g., neramexane or a pharmaceutically acceptable salt thereof such as neramexane mesylate) is administered in an immediate release formulation or a modified release formulation.

A further aspect of the invention relates to the above-defined derivative or use wherein the 1-amino-alkylcyclohexane derivative (e.g., neramexane or a pharmaceutically acceptable salt thereof such as neramexane mesylate) is administered in a topical formulation such as a topical rinse-off or leave-on formulation.

A further aspect of the invention relates to the above-defined derivative or use wherein the 1-amino-alkylcyclohexane derivative (e.g., neramexane or a pharmaceutically acceptable salt thereof such as neramexane mesylate) is administered between 0.1 and 99% by weight of the formulation.

A further aspect of the invention relates to the above-defined derivative or use wherein the 1-amino-alkylcyclohexane derivative (e.g., neramexane or a pharmaceutically acceptable salt thereof such as neramexane mesylate) is administered in an oral formulation.

A further aspect of the invention relates to the above-defined derivative or use wherein the 1-amino-alkylcyclohexane derivative (e.g., neramexane or a pharmaceutically acceptable salt thereof such as neramexane mesylate) is administered systemically.

A further aspect of the invention relates to the above-defined derivative or use wherein at least one additional pharmaceutical agent (e.g., antimicrobial agents, antibiotics, retinoids or steroids) which has been shown to be effective in treating or preventing inflammatory skin diseases is administered.

A further aspect of the invention relates to the above-defined derivative or use wherein the 1-amino-alkylcyclohexane derivative (e.g., neramexane or a pharmaceutically acceptable salt thereof such as neramexane mesylate) and the additional pharmaceutical agent (e.g., antimicrobial agents, antibiotics, retinoids or steroids) are administered conjointly.

A further aspect of the invention relates to the above-defined derivative or use wherein the 1-amino-alkylcyclohexane derivative (e.g., neramexane or a pharmaceutically acceptable salt thereof such as neramexane mesylate) and the additional pharmaceutical agent (e.g., antimicrobial agents, antibiotics, retinoids or steroids) are administered in a single formulation.

A further aspect of the invention relates to the above-defined derivative or use wherein the 1-amino-alkylcyclohexane derivative (e.g., neramexane or a pharmaceutically acceptable salt thereof such as neramexane mesylate) and the additional pharmaceutical agent (e.g., antimicrobial agents, antibiotics, retinoids or steroids) are administered in a topical formulation such as a topical rinse-off or leave-on formulation.

A further aspect of the invention relates to the above-defined derivative or use wherein the 1-amino-alkylcyclohexane derivative (e.g., neramexane or a pharmaceutically acceptable salt thereof such as neramexane mesylate) and the additional pharmaceutical agent (e.g., antimicrobial agents, antibiotics, retinoids or steroids) are administered in an oral formulation.

A further aspect of the invention relates to the above-defined derivative or use wherein the 1-amino-alkylcyclohexane derivative (e.g., neramexane or a pharmaceutically acceptable salt thereof such as neramexane mesylate) and the additional pharmaceutical agent (e.g., antimicrobial agents, antibiotics, retinoids or steroids) are administered systemically.

A further aspect of the invention relates to a pharmaceutical composition for the treatment of inflammatory skin diseases comprising a therapeutically effective amount of a 1-amino-alkylcyclohexane derivative (e.g., neramexane or a pharmaceutically acceptable salt thereof such as neramexane mesylate), and, optionally, at least one pharmaceutically acceptable carrier or excipient.

A further aspect of the invention relates to a pharmaceutical composition for the treatment of inflammatory skin diseases comprising a therapeutically effective amount of a 1-amino-alkylcyclohexane derivative (e.g., neramexane or a pharmaceutically acceptable salt thereof such as neramexane mesylate) in an immediate or modified release formulation.

A further aspect of the invention relates to a pharmaceutical composition comprising a therapeutically effective amount of a 1-amino-alkylcyclohexane derivative (e.g., neramexane or a pharmaceutically acceptable salt thereof such as neramexane mesylate) in a topical formulation.

A further aspect of the invention relates to a pharmaceutical composition for the treatment of inflammatory skin diseases comprising a therapeutically effective amount of a 1-amino-alkylcyclohexane derivative (e.g., neramexane or a pharmaceutically acceptable salt thereof such as neramexane mesylate) in a topical formulation.

A further aspect of the invention relates to a pharmaceutical composition for the treatment of inflammatory skin diseases comprising a therapeutically effective amount of a 1-amino-alkylcyclohexane derivative (e.g., neramexane or a pharmaceutically acceptable salt thereof such as neramexane mesylate) in an oral formulation.

A further aspect of the invention relates to a pharmaceutical composition comprising a therapeutically effective amount of a 1-amino-alkylcyclohexane derivative (e.g., neramexane or a pharmaceutically acceptable salt thereof such as neramexane mesylate) in combination with at least one additional pharmaceutical agent (e.g., antimicrobial agents, antibiotics, retinoids or steroids) which has been shown to be effective in treating inflammatory skin diseases and, optionally, at least one pharmaceutically acceptable carrier or excipient.

A further aspect of the invention relates to a pharmaceutical composition comprising a therapeutically effective amount of a 1-amino-alkylcyclohexane derivative (e.g., neramexane or a pharmaceutically acceptable salt thereof such as neramexane mesylate) in combination with at least one additional pharmaceutical agent (e.g., antimicrobial agents, antibiotics, retinoids or steroids) which has been shown to be effective in treating or preventing inflammatory skin diseases and, optionally, at least one pharmaceutically acceptable carrier or excipient.

A further aspect of the invention relates to a pharmaceutical composition comprising a therapeutically effective amount of a 1-amino-alkylcyclohexane derivative (e.g., neramexane or a pharmaceutically acceptable salt thereof such as neramexane mesylate) in combination with at least one additional pharmaceutical agent (e.g., antimicrobial agents, antibiotics, retinoids, steroids, or other non-specific agents) which has been shown to be effective in treating or preventing acne and, optionally, at least one pharmaceutically acceptable carrier or excipient.

A further aspect of the invention relates to a pharmaceutical composition comprising a therapeutically effective amount of a 1-amino-alkylcyclohexane derivative (e.g., neramexane or a pharmaceutically acceptable salt thereof such as neramexane mesylate) in combination with at least one additional pharmaceutical agent (e.g., antimicrobial agents, antibiotics, retinoids or steroids) which has been shown to be effective in treating inflammatory skin diseases and, optionally, at least one pharmaceutically acceptable carrier or excipient in the form of a topical or oral formulation.

A further aspect of the invention relates to a pharmaceutical composition comprising a therapeutically effective amount of a 1-amino-alkylcyclohexane derivative (e.g., neramexane or a pharmaceutically acceptable salt thereof such as neramexane mesylate) in combination with at least one additional pharmaceutical agent (e.g., antimicrobial agents, antibiotics, retinoids or steroids) which has been shown to be effective in treating or preventing inflammatory skin diseases and, optionally, at least one pharmaceutically acceptable carrier or excipient in the form of a topical or oral formulation.

A further aspect of the invention relates to a pharmaceutical composition comprising a therapeutically effective amount of a 1-amino-alkylcyclohexane derivative (e.g., neramexane or a pharmaceutically acceptable salt thereof such as neramexane mesylate) in combination with at least one additional pharmaceutical agent (e.g., antimicrobial agents, antibiotics, retinoids or steroids) which has been shown to be effective in treating or preventing acne and, optionally, at least one pharmaceutically acceptable carrier or excipient in the form of a topical or oral formulation.

A further aspect of the invention relates to a 1-amino-alkylcyclohexane derivative (e.g., neramexane or a pharmaceutically acceptable salt thereof such as neramexane mesylate) for reducing secretion of sebum and/or regulating composition of sebum.

A further aspect of the invention relates to the use of a 1-amino-alkylcyclohexane derivative (e.g., neramexane or a pharmaceutically acceptable salt thereof such as neramexane mesylate) for the manufacture of a medicament for reducing secretion of sebum and/or regulating composition of sebum.

A further aspect of the invention relates to the above-defined derivative or use wherein the 1-amino-alkylcyclohexane derivative (e.g., neramexane or a pharmaceutically acceptable salt thereof such as neramexane mesylate) is administered in a topical formulation such as a topical rinse-off or leave-on formulation.

A further aspect of the invention relates to a method of reducing secretion of sebum and/or regulating composition of sebum in a subject in need thereof, comprising administering to the individual an effective amount of a 1-amino-alkylcyclohexane derivative (e.g., neramexane or a pharmaceutically acceptable salt thereof such as neramexane mesylate).

A further aspect of the invention relates to such a method wherein the 1-amino-alkylcyclohexane derivative (e.g., neramexane or a pharmaceutically acceptable salt thereof such as neramexane mesylate) is administered in a topical formulation such as a topical rinse-off or leave-on formulation.

DETAILED DESCRIPTION OF THE INVENTION

Figure 1:
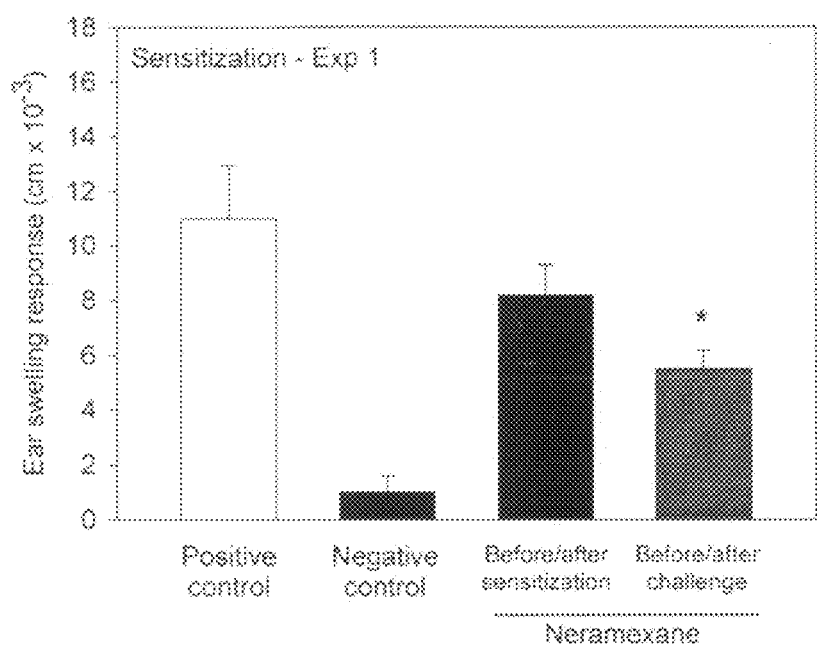
FIGS. 1-3 show the effects of neramexane in a contact hypersensitivity mouse model.

As used herein, the term inflammatory skin diseases includes acne, eczema, atopic dermatitis, rosacea, psoriasis and oily skin.

As used herein, the term inflammatory skin diseases also includes impetigo contagiosa.

As used herein, the term impetigo contagiosa includes bullous impetigo and ecthyma.

As used herein, the term acne includes acne vulgaris, persistent acne, and clinical acne.

As used herein, the term rosacea includes persistent edema of rosacea, rosacea conglobata, rosacea fulminans, ophthalmic rosacea, lupoid or granulomatous rosacea, steroid rosacea, gram-negative rosacea, halogen rosacea, phymas in rosacea, erythematotelangiectatic rosacea, papulopustular rosacea, phymatous rosacea and ocular rosacea.

As used herein, the term eczema includes atopic eczema, irritant contact dermatitis, allergic contact dermatitis, occupational dermatitis, xerotic eczema, seborrhoeic dermatitis, syshidrosis, discoid eczema, venous eczema, dermatitis herpetiformis, neurodermatitis, and autoeczematization.

As used herein, the term psoriasis includes psoriasis vulgaris, plaque psoriasis, flexural psoriasis, inverse psoriasis, guttate psoriasis, pustular psoriasis, nail psoriasis, erythrodermic psoriasis and psoriatic arthritis.

As used herein, the term antimicrobial agents include topical antimicrobial agents such as BPO, triclosan, chlorhexidine, salicylic acid, sulphur, resorcinol, and optical isomers, diastereomers, enantiomers, hydrates, their pharmaceutically acceptable salts, and mixtures thereof.

As used herein, the term antibiotics include topical antibiotics and oral antibiotics.

As used herein, the term topical antibiotics include erythromycin, clindamycin, tetracycline, metronidazole, and optical isomers, diastereomers, enantiomers, hydrates, their pharmaceutically acceptable salts, and mixtures thereof.

As used herein, the term oral antibiotics include erythromycin, tetracycline, oxytetracycline, doxycycline, minocycline, lymecycline, trimethoprim, and optical isomers, diastereomers, enantiomers, hydrates, their pharmaceutically acceptable salts, and mixtures thereof.

As used herein, the term retinoids include topical retinoids and oral retinoids such as isotretinoin and optical isomers, diastereomers, enantiomers, hydrates, and its pharmaceutically acceptable salts.

As used herein, the term topical retinoids include retinol, tretinoin, isotretinoin, motretinide, adapalene, tazarotene, and optical isomers, diastereomers, enantiomers, hydrates, their pharmaceutically acceptable salts, and mixtures thereof.

As used herein, the term steroids include spironolactone, drospirenone, cyproterone, cyproterone acetate, and optical isomers, diastereomers, enantiomers, hydrates, their pharmaceutically acceptable salts, and mixtures thereof.

As used herein, the term "subject" encompasses mammals including animals and humans.

The term 1-amino-alkylcyclohexane derivative is used herein to describe a 1-amino-alkylcyclohexane or a compound derived from 1-amino-alkylcyclohexane, e.g., pharmaceutically acceptable salts of 1-amino-alkylcyclohexanes.

The 1-amino-alkylcyclohexane derivatives of the present invention may be represented by the general formula (I):

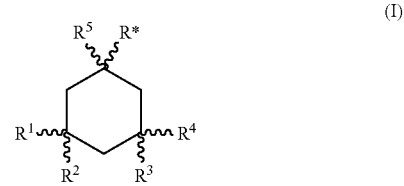

wherein $R^*$ is $-(CH_2)_n-(CR^6R^7)_m-NR^8R^9$
wherein $n+m=0$, 1, or 2
wherein $R^1$ through $R^7$ are independently selected from the group consisting of hydrogen and $C_{1-6}$alkyl, wherein $R^8$ and $R^9$ are independently selected from the group consisting of hydrogen and $C_{1-6}$alkyl or together represent lower-alkylene $-(CH_2)_x-$ wherein x is 2 to 5, inclusive, and optical isomers, enantiomers, hydrates, and pharmaceutically-acceptable salts thereof.

Non-limiting examples of the 1-amino-alkylcyclohexanes used according to the present invention include:
1-amino-1,3,5-trimethylcyclohexane,
1-amino-1(trans),3(trans),5-trimethylcyclohexane,
1-amino-1 (cis),3(cis),5-trimethylcyclohexane,
1-amino-1,3,3,5-tetramethylcyclohexane,
1-amino-1,3,3,5,5-pentamethylcyclohexane (neramexane),
1-amino-1,3,5,5-tetramethyl-3-ethylcyclohexane,
1-amino-1,5,5-trimethyl-3,3-diethylcyclohexane,
1-amino-1,5,5-trimethyl-cis-3-ethylcyclohexane,
1-amino-(1S,5S)cis-3-ethyl-1,5,5-trimethylcyclohexane,
1-amino-1,5,5-trimethyl-trans-3-ethylcyclohexane,
1-amino-(1R,5S)trans-3-ethyl-1,5,5-trimethylcyclohexane,
1-amino-1-ethyl-3,3,5,5-tetramethylcyclohexane,
1-amino-1-propyl-3,3,5,5-tetramethylcyclohexane,
N-methyl-1-amino-1,3,3,5,5-pentamethylcyclohexane,
N-ethyl-1-amino-1,3,3,5,5-pentamethyl-cyclohexane,
N-(1,3,3,5,5-pentamethylcyclohexyl)pyrrolidine,
3,3,5,5-tetramethylcyclohexylmethylamine,
1-amino-1-propyl-3,3,5,5-tetramethylcyclohexane,
1 amino-1,3,3,5(trans)-tetramethylcyclohexane (axial amino group),
3-propyl-1,3,5,5-tetramethylcyclohexylamine semihydrate,
1-amino-1,3,5,5-tetramethyl-3-ethylcyclohexane,
1-amino-1,3,5-trimethylcyclohexane,
1-amino-1,3-dimethyl-3-propylcyclohexane,
1-amino-1,3(trans),5(trans)-trimethyl-3(cis)-propylcyclohexane,
1-amino-1,3-dimethyl-3-ethylcyclohexane,
1-amino-1,3,3-trimethylcyclohexane,
cis-3-ethyl-1(trans)-3(trans)-5-trimethylcyclohexamine,
1-amino-1,3(trans)-dimethylcyclohexane,
1,3,3-trimethyl-5,5-dipropylcyclohexylamine,
1-amino-1-methyl-3(trans)-propylcyclohexane,
1-methyl-3(cis)-propylcyclohexylamine,
1-amino-1-methyl-3(trans)-ethylcyclohexane,
1-amino-1,3,3-trimethyl-5(cis)-ethylcyclohexane,
1-amino-1,3,3-trimethyl-5(trans)-ethylcyclohexane,
cis-3-propyl-1,5,5-trimethylcyclohexylamine,
trans-3-propyl-1,5,5-trimethylcyclohexylamine,
N-ethyl-1,3,3,5,5-pentamethylcyclohexylamine,
N-methyl-1-amino-1,3,3,5.5-pentamethylcyclohexane,
1-amino-1-methylcyclohexane,
N,N-dimethyl-1-amino-1,3,3,5,5-pentamethylcyclohexane,
2-(3,3,5,5-tetramethylcyclohexyl)ethylamine,
2-methyl-1-(3,3,5,5-tetramethylcyclohexyl)propyl-2-amine,
2-(1,3,3,5,5-pentamethylcyclohexyl-l)-ethylamine semihydrate,
N-(1,3,3,5,5-pentamethylcyclohexyl)-pyrrolidine,
1-amino-1,3(trans),5(trans)-trimethylcyclohexane,
1-amino-1,3(cis),5(cis)-trimethylcyclohexane,
1-amino-(1R,5S)trans-5-ethyl-1,3,3-trimethylcyclohexane,
1-amino-(1S,5S)cis-5-ethyl-1,3,3-trimethylcyclohexane,
1-amino-1,5,5-trimethyl-3(cis)-isopropyl-cyclohexane,
1-amino-1,5,5-trimethyl-3(trans)-isopropyl-cyclohexane,
1-amino-1-methyl-3(cis)-ethyl-cyclohexane,
1-amino-1-methyl-3(cis)-methyl-cyclohexane,
1-amino-5,5-diethyl-1,3,3-trimethyl-cyclohexane,
1-amino-1,3,3,5,5-pentamethylcyclohexane,
1-amino-1,5,5-trimethyl-3,3-diethylcyclohexane,
1-amino-1-ethyl-3,3,5,5-tetramethylcyclohexane,
N-ethyl-1-amino-1,3,3,5,5-pentamethylcyclohexane,
N-(1,3,5-trimethylcyclohexyl)pyrrolidine or piperidine,
N-[1,3(trans),5(trans)-trimethylcyclohexyl]pyrrolidine or piperidine,
N-[1,3(cis),5(cis)-trimethylcyclohexyl]pyrrolidine or piperidine,
N-(1,3,3,5-tetramethylcyclohexyl)pyrrolidine or piperidine,
N-(1,3,3,5,5-pentamethylcyclohexyl)pyrrolidine or piperidine,
N-(1,3,5,5-tetramethyl-3-ethylcyclohexyl)pyrrolidine or piperidine,
N-(1,5,5-trimethyl-3,3-diethylcyclohexyl)pyrrolidine or piperidine,
N-(1,3,3-trimethyl-cis-5-ethylcyclohexyl)pyrrolidine or piperidine,
N-[(1S,5S)cis-5-ethyl-1,3,3-trimethylcyclohexyl]pyrrolidine or piperidine,
N-(1,3,3-trimethyl-trans-5-ethylcyclohexyl)pyrrolidine or piperidine,
N-[(1R,5S)trans-5-ethyl,3,3-trimethylcyclohexyl]pyrrolidine or piperidine,
N-(1-ethyl-3,3,5,5-tetramethylcyclohexyl)pyrrolidine or piperidine,
N-(1-propyl-3,3,5,5-tetramethylcyclohexyl)pyrrolidine or piperidine,
N-(1,3,3,5,5-pentamethylcyclohexyl)pyrrolidine,
and optical isomers, diastereomers, enantiomers, hydrates, their pharmaceutically acceptable salts, and mixtures thereof.

1-Amino-alkylcyclohexane derivatives (e.g., neramexane, 1-amino-1,3,3,5,5-pentamethylcyclohexane) are disclosed in U.S. Pat. Nos. 6,034,134 and 6,071,966. 1-Amino-alkylcyclohexane derivatives (e.g., neramexane) may be used according to the invention in the form of any of pharmaceutically acceptable salts, solvates, isomers, conjugates, and prodrugs, any references to 1-amino-alkylcyclohexane derivatives (e.g., neramexane) in this description should be understood as also referring to such salts, solvates, isomers, conjugates, and prodrugs.

Pharmaceutically acceptable salts include, but are not limited to, acid addition salts, such as those made with hydrochloric, methylsulfonic, hydrobromic, hydroiodic, perchloric, sulfuric, nitric, phosphoric, acetic, propionic, glycolic, lactic, pyruvic, malonic, succinic, fumaric, tartaric, citric, benzoic, carbonic, cinnamic, mandelic, methanesulfonic, ethanesulfonic, hydroxyethanesulfonic, benzenesulfonic, p-toluene sulfonic, cyclohexanesulfamic, salicyclic, p-aminosalicylic, 2-phenoxybenzoic, and 2-acetoxybenzoic acid. All of these salts (or other similar salts) may be prepared by conventional means. The nature of the salt is not critical, provided that it is non-toxic and does not substantially interfere with the desired pharmacological activity.

The term "analog" or "derivative" is used herein in the conventional pharmaceutical sense, to refer to a molecule that structurally resembles a reference molecule (such as neramexane), but has been modified in a targeted and controlled manner to replace one or more specific substituents of the reference molecule with an alternate substituent, thereby generating a molecule which is structurally similar to the reference molecule. Synthesis and screening of analogs (e.g., using structural and/or biochemical analysis), to identify slightly modified versions of a known compound which may have improved or biased traits (such as higher potency and/or selectivity at a specific targeted receptor type, greater ability to penetrate mammalian barriers, such as cell membranes, fewer side effects, etc.) is a drug design approach that is well known in pharmaceutical chemistry.

The term "treat" is used herein to mean to relieve or alleviate at least one symptom of a disease in a subject. Within the meaning of the present invention, the term "treat" also denotes to arrest, delay the onset (i.e., the period prior to clinical manifestation of a disease) and/or reduce the risk of developing or worsening a disease.

The term "therapeutically effective" applied to dose or amount refers to that quantity of a compound or pharmaceutical composition that is sufficient to result in a desired activity upon administration to a mammal in need thereof.

The phrase "pharmaceutically acceptable", as used in connection with compositions of the invention, refers to molecular entities and other ingredients of such compositions that are physiologically tolerable and do not typically produce untoward reactions when administered to a mammal (e.g., human). The term "pharmaceutically acceptable" may also mean approved by a regulatory agency of the Federal or a state government or listed in the U.S. Pharmacopeia or other generally recognized pharmacopeia for use in mammals, and more particularly in humans.

The term "carrier" applied to pharmaceutical compositions of the invention refers to a diluent, excipient, or vehicle with which an active compound (e.g., neramexane) is administered. Such pharmaceutical carriers can be liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described e.g. in "Remington's Pharmaceutical Sciences" by A. R. Gennaro, 20$^{th}$ Edition.

The term "about" or "approximately" usually means within 20%, alternatively within 10%, including within 5% of a given value or range. Alternatively, especially in biological systems, the term "about" means within about a log (i.e., an order of magnitude), including within a factor of two of a given value.

Pharmaceutical Formulations and Administration

In conjunction with the methods of the present invention, also provided are pharmaceutical compositions comprising a therapeutically effective amount of a 1-amino-alkylcyclohexane derivative (e.g., neramexane). The compositions of the invention may further comprise a carrier or excipient (all pharmaceutically acceptable). The compositions may be formulated for once-a-day administration, twice-a-day administration, or three times a day administration.

The active ingredient (e.g., neramexane, such as neramexane mesylate) or the composition of the present invention may be used for the treatment of at least one of the mentioned disorders, wherein the treatment is adapted to or appropriately prepared for a specific administration as disclosed herein (e.g., to once-a-day, twice-a-day, or three times a day administration). For this purpose the package leaflet and/or the patient information contains corresponding information.

The active ingredient (e.g., neramexane, such as neramexane mesylate) or the composition of the present invention may be used for the manufacture of a medicament for the treatment of at least one of the mentioned disorders, wherein the medicament is adapted to or appropriately prepared for a specific administration as disclosed herein (e.g., to once-a-day, twice-a-day, or three times a day administration). For this purpose the package leaflet and/or the patient information contains corresponding information.

According to the present invention, the dosage form of the 1-amino-alkylcyclohexane derivative (e.g., neramexane) may be a solid, semisolid, or liquid formulation according to the following.

The 1-amino-alkylcyclohexane derivatives of the present invention (e.g., neramexane) may be administered orally, topically, parenterally, or mucosally (e.g., buccally, by inhalation, or rectally) in dosage unit formulations containing conventional non-toxic pharmaceutically acceptable carriers.

In another embodiment for administration to pediatric subjects, the 1-amino-alkylcyclohexane derivative may be formulated as a flavored liquid (e.g., peppermint flavor). The 1-amino-alkylcyclohexane derivatives of the present invention may be administered orally in the form of a capsule, a tablet, or the like, or as a liquid formulation or topically as a semi-solid such as an ointment, cream, gel, hydrogel (see Remington's Pharmaceutical Sciences, 20$^{th}$ Edition, by A. R. Gennaro).

For oral administration in the form of a tablet or capsule, the 1-amino-alkylcyclohexane derivatives of the present invention (e.g., neramexane) may be combined with non-toxic, pharmaceutically acceptable excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethyleneglycol, waxes, and the like.

The tablets may be coated with a concentrated sugar solution which may contain e.g., gum arabic, gelatine, talcum, titanium dioxide, and the like. Alternatively, the tablets can be coated with a polymer that dissolves in a readily volatile organic solvent or mixture of organic solvents. In specific embodiments, neramexane is formulated in immediate-release (IR) or modified-release (MR) dosage forms. Immediate release solid dosage forms permit the release of most or all of the active ingredient over a short period of time, such as 60 minutes or less, and make rapid absorption of the drug possible (immediate release formulations of 1-amino-alkylcyclohexanes such as neramexane are disclosed in US Published Application Nos. 2006/0002999 and 2006/0198884, the subject matter of which is hereby incorporated by reference). Modified release solid oral dosage forms permit the sustained release of the active ingredient over an extended period of time in an effort to maintain therapeutically effective plasma levels over similarly extended time intervals and/or to modify other pharmacokinetic properties of the active ingredient (modified release formulations of neramexane are disclosed in US Published Application No. 2007/0141148, the subject matter of which is hereby incorporated by reference).

For the formulation of soft gelatin capsules, the 1-amino-alkylcyclohexane derivatives of the present invention (e.g., neramexane) may be admixed with e.g., a vegetable oil or poly-ethylene glycol. Hard gelatin capsules may contain granules of the active substances using either the above mentioned excipients for tablets e.g., lactose, saccharose, sorbitol, mannitol, starches (e.g., potato starch, corn starch or amylopectin), cellulose derivatives or gelatine. Also liquids or semisolids of the drug can be filled into hard gelatine capsules.

The 1-amino-alkylcyclohexane derivatives of the present invention (e.g., neramexane) can also be introduced in microspheres or microcapsules, e.g., fabricated from polyglycolic acid/lactic acid (PGLA) (see, e.g., U.S. Pat. Nos. 5,814,344; 5,100,669 and 4,849,222; PCT Publications No. WO 95/11010 and WO 93/07861). Biocompatible polymers may be used in achieving controlled release of a drug, include for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

Formulation of the 1-amino-alkylcyclohexane derivatives of the present invention in a semi-solid or liquid form may also be used. The 1-amino-alkylcyclohexane derivative (e.g., neramexane) may constitute between 0.1 and 99% by weight of the formulation, more specifically between 0.5 and 20% by weight for formulations intended for injection and between 0.2 and 50% by weight for formulations suitable for oral administration.

Formulations of the 1-amino-alkylcyclohexane derivatives of the present invention in a semi-solid or liquid form suitable for topical administration may also be used.

Alternatively, formulations of the 1-amino-alkylcyclohexane derivatives of the present invention in a dry (solid) suitable for topical administration may be used.

Such formulations include gels, creams, ointments, hydrogels, pastes, emulsions, sprays, solutions, lotions, etc.

Such formulations also include powders, oleogels, suspensions, oil in water emulsions, water in oil emulsions, multiple emulsions, micro- and nanoemulsions, self emulsifying systems, aqueous and non aqueous solutions, patches, or transdermal systems. Combinations of the above-mentioned formulations may also be used.

The 1-amino-alkylcyclohexane derivative (e.g., neramexane) may constitute between 0.1 and 99% by weight of the formulation, more specifically between 0.5% and 50% by weight of the formulation or between 1% and 25% by weight of the formulation or between 2% and 20% by weight of the formulation.

In one embodiment of the invention, the 1-amino-alkylcyclohexane derivative (e.g., neramexane) is administered in a modified release formulation. Modified release dosage forms provide a means for improving patient compliance and for ensuring effective and safe therapy by reducing the incidence of adverse drug reactions. Compared to immediate release dosage forms, modified release dosage forms can be used to prolong pharmacologic action after administration, and to reduce variability in the plasma concentration of a drug throughout the dosage interval, thereby eliminating or reducing sharp peaks.

A modified release dosage form may comprise a core either coated with or containing a drug. The core is then coated with a release modifying polymer within which the drug is dispersed. The release modifying polymer disintegrates gradually, releasing the drug over time. Thus, the outer-most layer of the composition effectively slows down and thereby regulates the diffusion of the drug across the coating layer when the composition is exposed to an aqueous environment, i.e. the gastrointestinal tract. The net rate of diffusion of the drug is mainly dependent on the ability of the gastric fluid to penetrate the coating layer or matrix and on the solubility of the drug itself.

In another embodiment of the invention, the 1-amino-alkylcyclohexane derivative (e.g., neramexane) is formulated in an oral, liquid formulation. Liquid preparations for oral administration can take the form of, for example, solutions, syrups, emulsions or suspensions, or they can be presented as a dry product for reconstitution with water or other suitable vehicle before use. Preparations for oral administration can be suitably formulated to give controlled or postponed release of the active compound. Oral liquid formulations of 1-amino-alkylcyclohexanes, such as neramexane, are described in PCT International Application No. PCT/US2004/037026, the subject matter of which is hereby incorporated by reference.

For oral administration in liquid form, 1-amino-alkylcyclohexane derivatives of the present invention (e.g., neramexane) may be combined with non-toxic, pharmaceutically acceptable inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (e.g. BHA, BHT, propyl gallate, sodium ascorbate, citric acid) can also be added to stabilize the dosage forms. For example, solutions may contain from about 0.2% to about 20% by weight of neramexane, with the balance being sugar and mixture of ethanol, water, glycerol and propylene glycol. Optionally, such liquid formulations may contain coloring agents, flavoring agents, sweetening agents and thickening agents, such as carboxymethyl-cellulose, or other excipients.

In another embodiment, a therapeutically effective amount of a 1-amino-alkylcyclohexane derivative (e.g., neramexane) is administered in an oral solution containing a preservative, a sweetener, a solubilizer, and a solvent. The oral solution may include one or more buffers, flavorings, or additional excipients. In a further embodiment, a peppermint or other flavoring is added to the neramexane derivative oral liquid formulation.

For administration by inhalation, 1-amino-alkylcyclohexane derivatives (e.g., neramexane) of the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Solutions for parenteral applications by injection may be prepared in an aqueous solution of a water-soluble pharmaceutically acceptable salt of the active substances, for example in a concentration of from about 0.5% to about 10% by weight. These solutions may also contain stabilizing agents and/or buffering agents and may conveniently be provided in various dosage unit ampoules.

The formulations of the invention may be delivered parenterally, i.e., by intravenous (i.v.), intracerebroventricular (i.c.v.), subcutaneous (s.c.), intraperitoneal (i.p.), intramuscular (i.m.), subdermal (s.d.), or intradermal (i.d.) administration, by direct injection, via, for example, bolus injection or continuous infusion. Formulations for injection can be presented in unit dosage form, e.g., in ampoules or in multi-dose containers, with an added preservative. Alternatively, the active ingredient may be in powder form for reconstitution with a suitable vehicle, e.g., sterile pyrogen-free water, before use.

The invention also provides a pharmaceutical pack or kit comprising one or more containers containing a 1-amino-alkylcyclohexane derivative (e.g., neramexane) and, optionally, more of the ingredients of the formulation. In a specific embodiment, neramexane is provided as an oral solution (2 mg/ml) for administration with the use of a 2 teaspoon capacity syringe (dosage KORC®). Each oral syringe has hatch marks for measurement, with lines on the right side of the syringe (tip down) representing tsp units, and those on the left representing ml units.

The optimal therapeutically effective amount may be determined experimentally, taking into consideration the exact mode of administration, from in which the drug is administered, the indication toward which the administration is directed, the subject involved (e.g., body weight, health, age, sex, etc.), and the preference and experience of the physician or veterinarian in charge.

Dosage units for rectal application may be solutions or suspensions or may be prepared in the form of suppositories or retention enemas comprising neramexane in a mixture with a neutral fatty base, or gelatin rectal capsules comprising the active substances in admixture with vegetable oil or paraffin oil.

Toxicity and therapeutic efficacy of the compositions of the invention may be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it may be expressed as the ratio $LD_{50}/ED_{50}$. Compositions that exhibit large therapeutic indices are preferred.

Suitable daily doses of the active compounds of the invention in therapeutic treatment of humans are about 0.01-10 mg/kg bodyweight on peroral administration and 0.001-10 mg/kg bodyweight on parenteral administration. For example, for adults, suitable daily doses of neramexane (e.g. neramexane mesylate) are within the range from about 5 mg to about 150 mg per day, such as from about 5 mg to about 120 mg, from about 5 mg to about 100 mg, or from about 5 mg to about 75 mg, or from about 5 mg to about 50 mg, such as 25 mg or 37.5 mg or 50 mg, per day. For example the daily dose may be body weight-adjusted such as 50 mg/day up to 90 kg body weight or 75 mg/day for patients with a body weight of ≧90 kg. An equimolar amount of another pharmaceutically acceptable salt, a solvate, an isomer, a conjugate, a prodrug or a derivative thereof, such as neramexane hydrochloride, is also suitable. For pediatric subjects aged 4-14, neramexane (e.g. neramexane mesylate) may be administered as an oral, liquid dosage form, at about 0.5 mg/day, up to a maximum dose of 10 mg/day.

The daily doses indicated herein may be administered, for example, as one or two dosing units once, twice or three times per day. Suitable doses per dosage unit may therefore be the daily dose divided (for example, equally) between the number of dosage units administered per day, and will thus typically be about equal to the daily dose or one half, one third, one quarter or one sixth thereof. Dosages per dosage unit may thus be calculated from each daily dosage indicated herein. A daily dose of 5 mg, for example may be seen as providing a dose per dosage unit of, for example, about 5 mg, 2.5 mg, 1.67 mg, 1.25 mg and 0.83 mg, depending upon the dosing regimen chosen. Correspondingly, a dosage of 150 mg per day corresponds to dosages per dosing unit of, for example, about 150 mg, 75 mg, 50 mg, 37.5 mg, and 25 mg for corresponding dosing regimens.

Treatment duration may be short-term, e.g., several weeks (for example 8-14 weeks), or long-term until the attending physician deems further administration no longer is necessary.

The 1-amino-alkylcyclohexane derivatives of the present invention (e.g., neramexane) may be administered as a monotherapy, or in combination with another agent prescribed for the treatment of inflammatory skin diseases.

The term "combination" applied to active ingredients is used herein to define a single pharmaceutical composition (formulation) comprising two active agents (e.g., a pharmaceutical composition comprising a 1-amino-alkylcyclohexane derivative, such as neramexane, and another agent prescribed for the treatment of inflammatory skin diseases) or two separate pharmaceutical compositions, each comprising an active agent (e.g. a pharmaceutical composition comprising a 1-amino-alkylcyclohexane derivative, such as neramexane, and another pharmaceutical composition comprising another agent prescribed for the treatment of inflammatory skin diseases), to be administered conjointly.

Within the meaning of the present invention, the term "conjoint administration" is used to refer to administration of 1-amino-alkylcyclohexane derivative, such as neramexane, and one or more additional active agents (e.g. another agent prescribed for the treatment of inflammatory skin diseases such as antimicrobial agents, antibiotics, retinoids or steroids) simultaneously in one composition, or simultaneously in different compositions, or sequentially. For the sequential administration to be considered "conjoint", however, 1-amino-alkylcyclohexane derivative, such as neramexane, and the one or more additional active agents must be administered separated by a time interval which still permits the resultant beneficial effect for treating inflammatory skin diseases in a mammal.

EXAMPLES OF REPRESENTATIVE FORMULATIONS

With the aid of commonly used solvents, auxiliary agents and carriers, active ingredients may be processed into tablets, coated tablets, capsules, drip solutions, suppositories, injection and infusion preparations, gels, creams, ointments, and the like and can be therapeutically applied by the oral, rectal, parenteral, topical, and additional routes. Tablets suitable for oral administration may be prepared by conventional tabletting techniques. The following example is given by way of illustration only and is not to be construed as limiting.

Formulation Example 1

Neramexane Mesylate Immediate Release Tablets

The following tables provide the make-up of neramexane immediate release tablets in 12.5, 25.0, 37.5, and 50.0 mg dosages, including active components, coating agents, and other excipients.

TABLE 1

Neramexane mesylate, 12.5 mg film coated tablets

| Component | Amount [mg] | Function |
|---|---|---|
| Neramexane mesylate | 12.50 | Active pharmaceutical ingredient |
| Cellulose microcrystalline | 103.25 | Binder |
| Croscarmellose sodium | 6.25 | Disintegrant |
| Silicon dioxide, colloidal | 1.25 | Flow promoter |
| Talc | 1.25 | Glident |
| Magnesium stearate | 0.50 | Lubricant |
| core weight | 125.00 | |
| Coating (HPMC), Opadry or Sepifilm | 5.00 | Coating |
| Coat weight | 5.00 | |
| coated tablet total weight | 130.00 | |

TABLE 2

Neramexane mesylate, 25.0 mg film coated tablets

| Component | Amount [mg] | Function |
|---|---|---|
| Neramexane mesylate | 25.00 | Active pharmaceutical ingredient |
| Cellulose microcrystalline | 206.50 | Binder |
| Croscarmellose sodium | 12.5 | Disintegrant |
| Silicon dioxide, colloidal | 2.50 | Flow promoter |
| Talc | 2.50 | Glident |
| Magnesium stearate | 1.00 | Lubricant |
| core weight | 250.00 | |
| Coating (HPMC), Opadry or Sepifilm | 10.00 | Coating |
| Coat weight | 10.00 | |
| coated tablet total weight | 260.00 | |

TABLE 3

Neramexane mesylate, 37.5 mg film coated tablets

| Component | Amount [mg] | Function |
|---|---|---|
| Neramexane mesylate | 37.50 | Active pharmaceutical ingredient |
| Cellulose microcrystalline | 309.75 | Binder |
| Croscarmellose sodium | 18.75 | Disintegrant |
| Silicon dioxide, colloidal | 3.75 | Flow promoter |
| Talc | 3.75 | Glident |
| Magnesium stearate | 1.50 | Lubricant |
| core weight | 375.00 | |
| Coating (HPMC), Opadry or Sepifilm | 15.00 | Coating |
| Coat weight | 15.00 | |
| coated tablet total weight | 390.00 | |

TABLE 4

Neramexane mesylate, 50.0 mg film coated tablets

| Component | Amount [mg] | Function |
|---|---|---|
| Neramexane mesylate | 50.00 | Active pharmaceutical ingredient |
| Cellulose microcrystalline | 413.00 | Binder |
| Croscarmellose sodium | 25.00 | Disintegrant |
| Silicon dioxide, colloidal | 5.00 | Flow promoter |
| Talc | 5.00 | Glident |
| Magnesium stearate | 2.00 | Lubricant |
| core weight | 500.00 | |
| Coating (HPMC), Opadry or Sepifilm | 20.00 | Coating |
| Coat weight | 20.00 | |
| coated tablet total weight | 520.00 | |

The following tables provide the make-up of Neramexane topical formulations.

Formulation Example 2

TABLE 5

"Unguentum emulsificans"

| Description | Amount |
|---|---|
| Alcohol cetylicus et stearylicus emulsificans | 30.0 g |
| Paraffinum subliquidum | 35.0 g |
| Vaselinum album | 35.0 g |

TABLE 6

"Unguentum emulsificans aquosum" containing 1% Neramexane

| Description | Amount |
|---|---|
| Neramexane mesylate | 1.0 g |
| Unguentum emulsificans | 30.0 g |
| Aqua purificata | 69.0 g |

TABLE 7

"Unguentum emulsificans aquosum" containing 20% Neramexane

| Description | Amount |
|---|---|
| Neramexane mesylate | 20.0 g |
| Unguentum emulsificans | 30.0 g |
| Aqua purificata | 50.0 g |

Formulation Example 3

TABLE 8

"Cremor nonionicus emulsificans aquosum"

| Description | Amount |
|---|---|
| Alcohol cetylicus et stearylicus emulsificans nonionicum | 21.0 g |
| 2-Ethylhexylis lauras | 10.0 g |
| Glycerolum 85% | 5.0 g |
| Kalium sorbinicum | 0.14 g |
| Acidum citricum, anhydricum | 0.07 g |
| Aqua purificata | 63.79 g |

TABLE 9

"Cremor nonionicus emulsificans aquosum" containing 1% Neramexane

| Description | Amount |
|---|---|
| Neramexane mesylate | 1.0 g |
| Cremor nonionicus emulsificans aquosum | 99.0 g |

TABLE 10

"Cremor nonionicus emulsificans aquosum" containing 10% Neramexane

| Description | Amount |
| --- | --- |
| Neramexane mesylate | 10.0 g |
| Cremor nonionicus emulsificans aquosum | 90.0 g |

Formulation Example 4

TABLE 11

"Macrogoli unguentum"

| Description | Amount |
| --- | --- |
| Macrogolum 300 | 50.0 g |
| Macrogolum 1500 | 50.0 g |

TABLE 12

"Macrogoli unguentum" containing 2% Neramexane

| Description | Amount |
| --- | --- |
| Neramexane mesylate | 2.0 g |
| Macrogoli unguentum | 98.0 g |

TABLE 13

"Macrogoli unguentum" containing 15% Neramexane

| Description | Amount |
| --- | --- |
| Neramexane mesylate | 15.0 g |
| Macrogoli unguentum | 85.0 g |

Formulation Example 5

TABLE 14

"Linimentum nonionicum aquosum"

| Description | Amount |
| --- | --- |
| Alcohol cetylicus et stearylicus emulsificans nonionicum | 10.5 g |
| 2-Ethylhexylis lauras | 5.0 g |
| Glycerolum 85% | 2.5 g |
| Kalium sorbinicum | 0.14 g |
| Acidum citricum, anhydricum | 0.07 g |
| Aqua purificata | 81.79 g |

TABLE 15

"Linimentum nonionicum aquosum" containing 3% Neramexane

| Description | Amount |
| --- | --- |
| Neramexane mesylate | 3.0 g |
| Linimentum nonionicum aquosum | 97.0 g |

TABLE 16

"Linimentum nonionicum aquosum" containing 12% Neramexane

| Description | Amount |
| --- | --- |
| Neramexane mesylate | 12.0 g |
| Linimentum nonionicum aquosum | 88.0 g |

TABLE 17

"Linimentum nonionicum aquosum" containing 25% Neramexane

| Description | Amount |
| --- | --- |
| Neramexane mesylate | 25.0 g |
| Linimentum nonionicum aquosum | 75.0 g |

EXAMPLES

The following examples illustrate the invention without limiting its scope.

Example 1

Effects of Neramexane in a Contact Hypersensitivity Mouse Model

The contact hypersensitivity model (CHS) induced by epicutaneous application of haptens serves as a model for a delayed type hypersensitivity reaction (Schwarz et al., 2004, The Journal of Immunology, 172:1036-1043). Antigen-specific T lymphocytes are induced which can be demonstrated by adoptive transfer experiments. Ear swelling response is only induced in mice which have been successfully sensitized, indicating that the response is an immune response and not a toxic reaction. Negative controls, i.e., mice which have not been sensitized, do not respond with ear swelling upon first application of the hapten on their ears. Since suppression of the sensitization by drugs may indicate immunosuppressive activity of the respective substance, the CHS model is utilized to screen drugs for immunosuppressive properties.

Although the ear swelling response (challenge) also reflects an immune response (T lymphocytes are the essential mediators), the ear swelling response is finally mediated via inflammatory cytokines which are induced by the antigen-specific T lymphocytes. Thus, the challenge of this immune reaction can also be suppressed by antiinflammatory drugs. Thus, the CHS model is utilized to measure antiinflammatory properties and also allows for a differentiation between substances with immunosuppressive and antiinflammatory properties.

Neramexane is tested for its efficacy in influencing immunologic and/or inflammatory reactions.

Materials and Methods

Animals

For this study C57BL/6N male mice (6-8 weeks, approximately 20 g) are used.

The animals are allowed to acclimatise for 5 days before the start of the study. There is automatic control of light cycle, temperature and humidity. Light cycles are 12 hours. Daily monitoring indicates that temperature and humidity remain within the target ranges of 21° C.±1° C. and 50±5%, respectively. The animals are housed in polypropylene cages (Ebeco, type M-3) with mesh tops (up to 7 mice are housed per cage). Cages, bedding, and water bottles are changed at regular intervals, i.e. every 7 days. Standard Diet (vendor) is available to the animals ad libitum. The animals have access to domestic quality mains water ad libitum.

Drugs

Neramexane mesylate is diluted with NaCl solution and freshly prepared for each injection, and dose levels are determined via a pharmacokinetic pilot study. Based on the pilot study, a dose of 5 mg/kg 1 hour before sensitization followed by a dose of 3.2 mg/kg injected 1 and 3 hours after sensitization is used.

Treatment

Upon arrival, all animals are randomly allocated to treatment groups, such that the treatment groups are evenly distributed throughout the caging system.

The treatment groups and animal numbers are arranged as shown in Table 18:

TABLE 18

| Group | Treatment Group | Dose Level $(mg \cdot kg^{-1} \cdot day^{-1})*$ | Number of Animals in Exp. 1, 2, 3 |
|---|---|---|---|
| 1 | Positive Control | 0 | 3, 5, 8 |
| 2 | Negative Control | 0 | 2, 3, 5 |
| 3 | Neramexane before sensitization | 5 mg/kg 1 hr before sensitization, 3.2 mg/kg 1 hr and 3.2 mg/kg 3 hr after sensitization | 6, 7, 8 |
| 4 | Neramexane before challenge | 5 mg/kg 1 hr before challenge, 3.2 mg/kg 1 hr and 3.2 mg/kg 3 hr after challenge | 6, 7, 8 |

Dose refers to free base/acid, the conversion factor from free base to salt form is 1.57.

The animals are injected intraperitoneally (i.p.) at a constant dose volume of 200 µl ml dosing solution per kg of body weight, using a steel dosing cannula. The volume administered to each animal is determined each day by the weight of that animal at the time of administration.

Mice are sensitized by painting 50 µl of dinitrofluorobenzene (DNFB, Sigma Corp., St. Louis, Mo.) solution (0.5% in acetone:olive oil, 4:1) on the shaved back on day 0. On day 5, 20 µl of 0.3% DNFB is applied to the left ear. Ear swelling is quantified with a spring-loaded micrometer 24 hours after elicitation. Contact hypersensitivity (CHS) is determined as the amount of swelling of the hapten-challenged ear compared to the thickness of the vehicle-treated ear and expressed in cm×$10^{-3}$ (mean±SD). For positive control, animals are sensitized with 50 µl of 0.5% DNFB through the shaved skin. Challenge is performed 5 days later on the left ear (0.3% DNFB, 20 µl). Ear thickness is measured 24 hours later (cm×$10^{-3}$). For negative control, mice are challenged with 0.3% DNFB, 20 µl and ear thickness is measured 24 hours later (cm×$10^{-3}$).

Evaluation of Data

Figure 2:
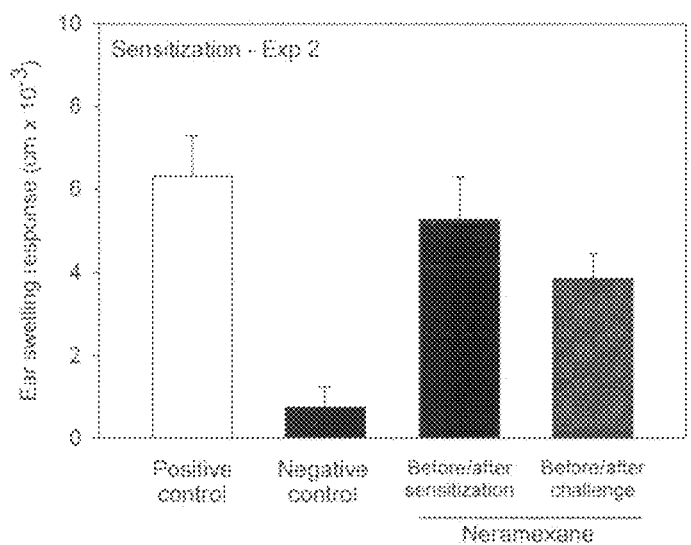
Figure 3:
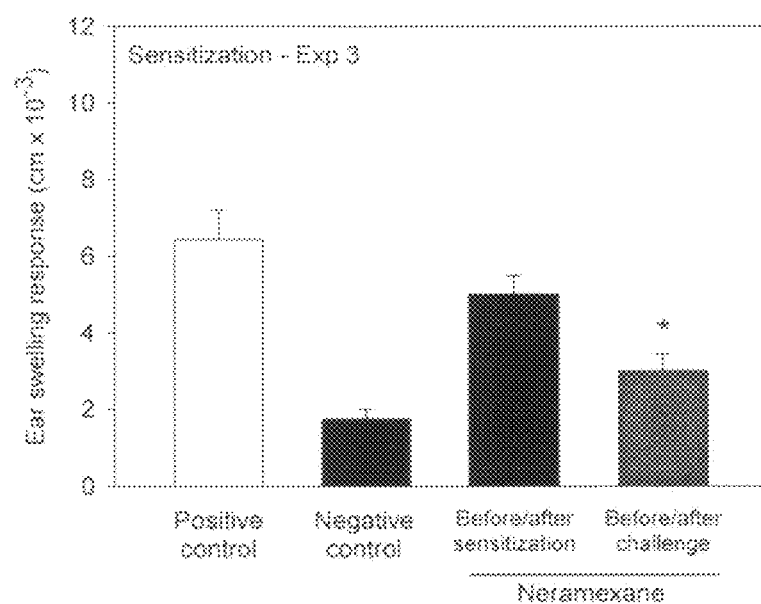

Sensitization results are analyzed using one way ANOVA (excluding negative control group) followed by Dunnett as post-hoc test. The results are shown in FIGS. 1-3

Results

Neramexane does not appear to have an impact on the induction of an immune response; however, administration of neramexane around challenge significantly reduces ear swelling response. These results indicate that neramexane may exert antiinflammatory but not immunosuppressive properties and that neramexane may be useful in treating inflammatory skin diseases such as acne, rosacea, eczema, atopic dermatitis, psoriasis and oily skin.

Example 2

Effects of Neramexane in a Dermatitis Mouse Model

In order to further test for antiinflammatory properties, an irritant dermatitis mouse model is used. Induction of an ear swelling response by croton oil is a toxic reaction. This response is a concentration-dependent phenomenon, independent of sensitized lymphocytes. Antiinflammatory substances have been shown to reduce the ear swelling response to a certain degree.

Neramexane is tested for its antiinflammatory properties.

Animals

For this study C57BL/6N male mice (6-8 weeks, approximately 20 g) are used.

The animals are allowed to acclimatise for 5 days before the start of the study. There is automatic control of light cycle, temperature and humidity. Light cycles are 12 hours. Daily monitoring indicates that temperature and humidity remain within the target ranges of 21° C.±1° C. and 50±5%, respectively. The animals are housed in polypropylene cages (Ebeco, type M-3) with mesh tops (up to 7 mice are housed per cage). Cages, bedding, and water bottles are changed at regular intervals, i.e. every 7 days. Standard Diet (vendor) is available to the animals ad libitum. The animals have access to domestic quality mains water ad libitum.

Drugs

Neramexane mesylate is diluted with NaCl solution and freshly prepared for each injection, and dose levels are determined via a pharmacokinetic pilot study. Based on the pilot study, a dose of 5 mg/kg 1 hour before sensitization followed by a dose of 3.2 mg/kg injected 1 and 3 hours after sensitization is used.

Treatment

Upon arrival, all animals are randomly allocated to treatment groups, such that the treatment groups are evenly distributed throughout the caging system.

The treatment groups and animal numbers are arranged as shown in Table 19:

TABLE 19

| Group | Treatment Group | Dose Level $(mg \cdot kg^{-1} \cdot day^{-1})*$ | Number of Animals in Exp. 1, 2 |
|---|---|---|---|
| 1 | Positive Control | 0 | 4, 7 |
| 2 | Negative Control | 0 | 2, 5 |
| 3 | Neramexane before irritation | 5 mg/kg 1 hr before irritation, 3.2 mg/kg 1 hr and 3.2 mg/kg 3 hr after irritation | 8, 8 |

Dose refers to free base/acid, the conversion factor from free base to salt form is 1.57.

The animals are injected intraperitoneally (i.p.) at a constant dose volume of 200 µl ml dosing solution per kg of body weight, using a steel dosing cannula. The volume administered to each animal is determined each day by the weight of that animal at the time of administration.

The animals are injected intraperitoneally (i.p.) at a constant dose volume of 200 µl ml dosing solution per kg of body weight, using a steel dosing cannula. The volume administered to each animal is determined each day by the weight of that animal at the time of administration.

20 μl of 1% croton oil in acetone is applied on the left ear. Ear swelling is measured after 7 hours and 24 hours. Ear swelling is quantified with a springloaded micrometer. Irritant reaction is determined as the amount of swelling of the irritant-treated ear compared to the thickness of the vehicle (acetone)-treated ear and expressed in cm×$10^{-3}$. An additional group is treated with neramexane (as described above) and croton oil.

Evaluation of Data

Figure 4:
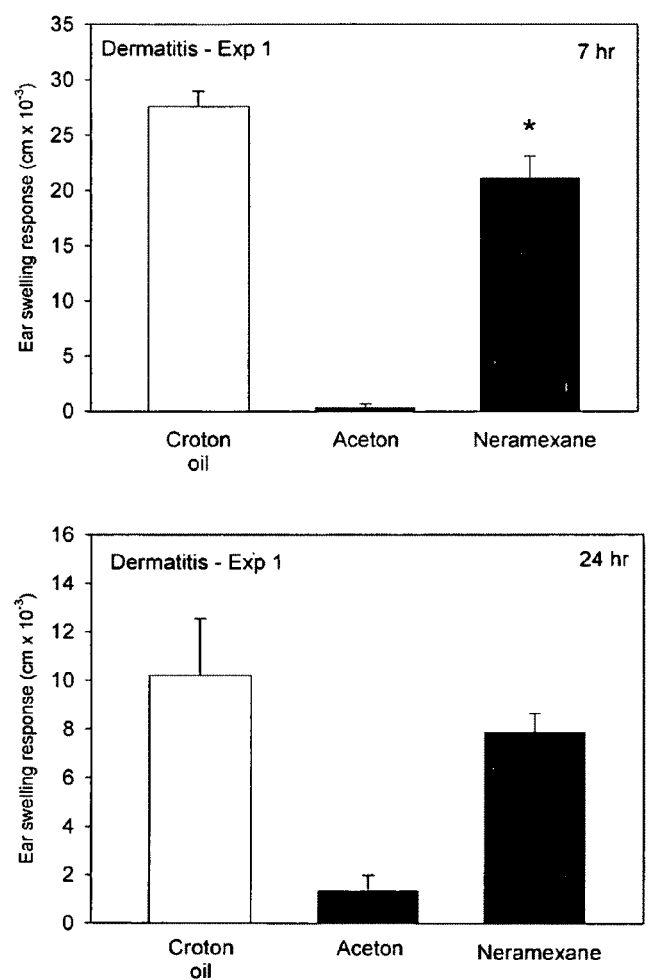
FIGS. 4-5 show the effects of neramexane in a dermatitis mouse model.
Figure 5:
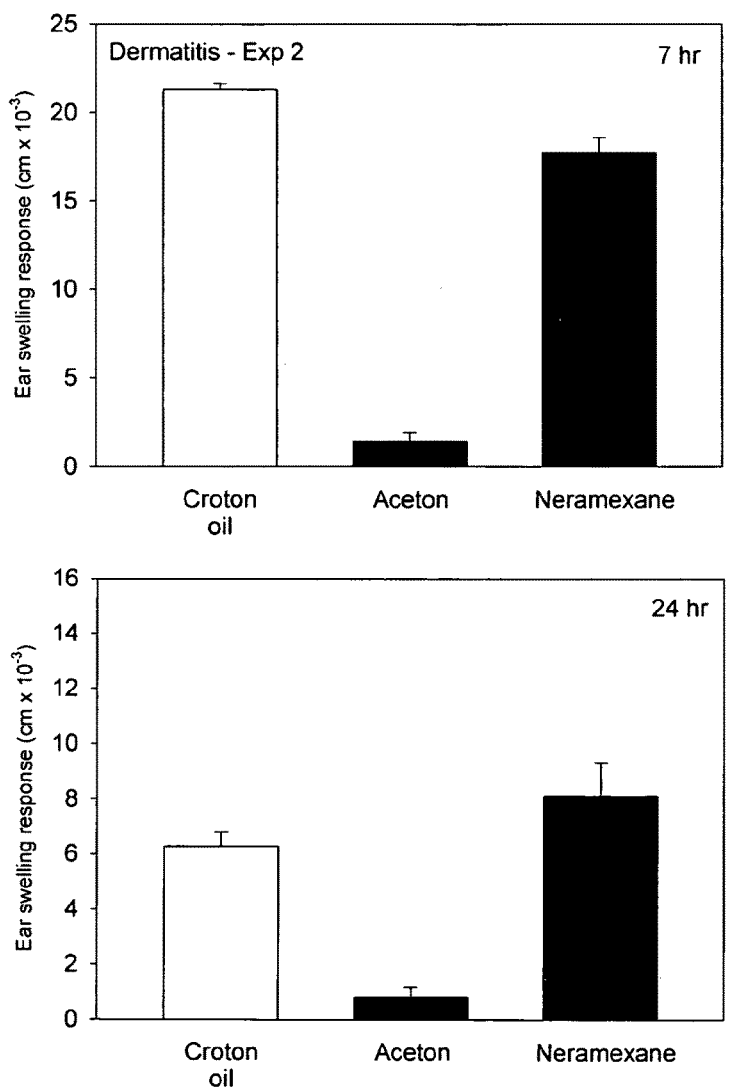

Sensitization results are analyzed using student test (comparison between treatment and positive control). The results are shown in FIGS. 4-5.

Results

Neramexane reduces the ear swelling response induced by croton oil to some degree, indicating that neramexane may be useful in the treatment of inflammatory skin diseases such as acne, rosacea, eczema, atopic dermatitis, psoriasis and oily skin.

Example 3

Antimicrobial Properties of Neramexane Against *Propionibacterium acnes*

In order to determine the efficacy of Neramexane against a specific microorganism population (i.e., *Propionibacterium acnes*), a log reduction assay is performed.

The organisms are prepared by inoculating the fluid thioglycolate (FTM). The microorganism is then incubated at 35.2±2.5° C. for 24 hours. The microbial suspension is adjusted to approximately $10^7$ to $10^8$ colony forming units (CFU) per mL and labeled as the stock suspension. An additional 1:10 dilution of the stock suspension is made using PBS to achieve a concentration of approximately $10^5$ to $10^6$ CFU per mL.

Neramexane mesylate (1 gram) is diluted into 9.0 mL of DI water to prepare a 10% solution (1:10 dilution). Then 5 mL is transferred into 11 mL of DI water to prepare a 3.125% solution. This solution is then inoculated with the microorganism and tested at time intervals of 30 seconds, 1 minute, and 5 minutes.

One milliliter from each dilution is spread plated in duplicate onto tryptic soy agar with 5% sheep blood. The plates are incubated anaerobically at 35.2±2.5° C. for a minimum of 48 hours. The same procedure is repeated for the Phosphate Buffer Saline control. After the incubation period, all plates are counted to determine the number of microorganisms remaining at each time point.

The concentration of each microorganism for the control and product is calculated for each interval. The log reduction is calculated to determine the change (reduction or increase) of the microorganism population relative to a starting inoculum. The minimum required bactericidal concentration is defined as a 3 log reduction from the initial inoculum. The results are shown in Table 20.

TABLE 20

| Exposure | Concentration of Organism (CFU/mL) | | % Reduction | | Log Reduction | |
|---|---|---|---|---|---|---|
| Time | Control | Product | Control | Product | Control | Product |
| Initial | 2.1E+05 | 2.1E+05 | N/A | N/A | N/A | N/A |
| 30 sec | 1.6E+05 | 1.8E+04 | 23.8 | 91.6 | 0.1 | 1.1 |
| 1 min | 1.6E+05 | 4.4E+04 | 23.8 | 79.0 | 0.1 | 0.7 |
| 5 min | 1.5E+05 | <10 | 28.6 | 100.0 | 0.1 | 4.3 |

Results

Based on the activity measured in the log reduction experiment, Neramexane exhibits antibacterial activity against *Propionibacterium acnes*. These results indicate that neramexane may be useful in the treatment of inflammatory skin diseases such as acne, rosacea, eczema, atopic dermatitis, psoriasis and oily skin.

Example 4

Local Tolerability of Topical Neramexane Formulation

The objective of this study is to evaluate the local tolerance of Neramexane mesylate in a topical formulation at different dose levels after 14 days of daily dermal treatment to minipigs.

The study is performed in 4 female Göttingen SPF minipigs (from Ellegaard Göttingen Minipigs Aps). Each animal has 5 application sites (25 cm$^2$) marked on the back and is dosed for 8 hours each day. Each test site is used for the same test item or placebo throughout the study. The test group is treated with Neramexane mesylate at the following concentrations: 0, 0.5, 2.5, 5.0 and 10.0% (w/w).

Clinical signs are recorded 2-4 hours post start of each treatment and the local dermal reactions (erythema, oedema) are evaluated prior to treatment. Body weight is recorded weekly (and also on Day 1 and at necropsy). Gross necropsy is performed on all animals, however no macroscopic changes are observed and therefore only the dermal application sites are collected and subsequently macroscopically and microscopically histopathological evaluation is performed.

No test item related changes are observed in relation to clinical signs and body weight gain of the animals. Furthermore, no test item related dermal skin reactions are observed throughout the study. The results from the histopathology evaluation of the dermal applications sites reveals no treatment-related macroscopic or microscopic findings as compared to the untreated skin samples.

In conclusion, dermal treatment of Göttingen minipigs for 14 Days with Neramexane mesylate at dose levels of and 0.5%, 2.5%, 5% and 10% in a topical formulation results in no test item related changes. Under the conditions of this study, the Neramexane topical formulation demonstrates a good local (topical) tolerability.

Example 5

Anti-Microbial Potency of Neramexane Against Relevant Bacterias—Determination of MIC and MBC Values by the Agar Dilution Method To assess the anti-microbial potency of Neramexane against acne relevant bacterias the minimal inhibitory concentration (MIC) and minimal bactericidal concentration (MBC) against the following bacterias is established:

| | | |
|---|---|---|
| 1. | *Staphylococcus epidermidis* | ATCC 12228 |
| 2. | *Propionibacterium acnes* | ATCC 11828 |
| 3. | *Propionibacterium granulosum* | ATCC 11829 |
| 4. | *Propionibacterium avidum* | ATCC 25577 |

Procedure

The MICs of the samples are determined using the agar dilution method based on DIN 58940. Petri dishes of 5.5 cm diameter are poured with 2.5 ml of freshly prepared Mueller-Hinton agar (Merck company, Cat-No 1.05437) or Wilkins-Chalgren-Agar (Oxoid company, Cat-No CM643), maintained in liquid form at 50° C., to which the sample dilutions at various concentrations have been added at 50.0 vol.-%.

Preparation of Test Solution and Agar Plates

For the different test compounds the following concentration ranges are tested:

| Testing product no. | Testing product name | Concentration range [%] |
|---|---|---|
| 1. | Neramexane-Mesylate | $6.25\text{-}1 * 10^{-2}$ |
| 2. | Neramexane-HCl | $1.56\text{-}2 * 10^{-3}$ |

To prepare the starting sample dilutions, a 12.5%, 3.12% suspension of the respective sample solution is prepared with Aqua purificata. From these stock-solutions, further dilutions are prepared with Aqua purificata. All test compounds are adjusted to pH 5.5. For test product no. 1, separate dilutions adjusted to pH 6.0 and pH 7.4 are also prepared.

Execution of the Agar Dilution Test

For inoculation, 1 µl of the respective germ suspension is placed on the centre of each agar plate. After drying, inoculated plates are incubated at 36.0±2.0° C. The basis for the length of incubation period is the respective growth control cultivated in parallel.

TABLE 21

Test Organisms and Microbial Counts of Test Microbe Suspensions

| No | Test Organisms | | CFU*/ml |
|---|---|---|---|
| 1 | *Propionibacterium acnes* | ATCC 11828 | $2.6 \times 10^8$ |
| 2 | *Propionibacterium avidum* | ATCC 25577 | $3.0 \times 10^8$ |
| 3 | *Propionibacterium granulosum* | ATCC 11829 | $3.9 \times 10^8$ |
| 4 | *Staphylococcus epidermidis* | ATCC 12228 | $1.9 \times 10^7$ |

*= colony forming units

The purity and identity of all test microorganisms is checked by preparation of subcultures on Columbia-Blood agar for germs no. 1-3 (anaerobic) and germ no. 4 (aerobic). Subsequently, the germs are identified by determination of the biochemical profile using ATB/API.

The test microbe suspension is prepared by inoculating a few individual colonies of the respective bacteria into sterile saline solution until a turbidity corresponding to the McFarland standard 1.0 (approximately $10^8$ cfu/ml) is reached. After that, the test microbe suspensions are further diluted 1:10 with saline solution and the microbial counts (see Table 21) are determined by the surface spread method using a spiral plater.

The agar plates are incubated under the conditions given in Table 22 and subsequently evaluated. The MIC-values as given represent the lowest concentration of the active substance at which there is no macroscopically visible growth. Minimal, barely visible growth or few small individual colonies are evaluated as inhibition.

TABLE 22

Inoculation and Incubation Conditions

| Test Organism No | Growth Conditions | Nutrient Medium | Incubation |
|---|---|---|---|
| 1-3 | anaerobic | Wilkins-Chalgren agar | 16-20 h at 36° C. |
| 4 | aerobic | Mueller-Hinton agar | 16-20 h at 36° C. |

Determination of the Minimal Bactericidal Concentration (MBC)

All negative tests of the determination of the minimal bactericidal concentration are the basis of verification of remaining germs, the inoculated agar segments are cut and put in Mueller-Hinton-Bouillon (germ 1) or Wilkins-Chalgren-Bouillon (germs 2-4). After an adequate incubation period at 36.0±2.0° C. (as judged from a control without test compound), the tests are checked manually on microbial growth (=turbidity) and the minimal bactericidal concentration is determined. MBC indicates the concentration without marked turbidity. Grown germs are checked for identity to rule out unspecific contaminations.

Evaluation of Data

The following results are summarized and tabulated:
a) Results of the Minimal Inhibitory Concentration (MIC)*
b) Results of the Minimal Bactericidal Concentration (MBC)

*The MIC is the concentration without macroscopical growth. Scarcely apparent, minimum growth or few single colonies are not considered. The controls must have a respectively good developed growth. There must be no growth on the agar plates for the sterile control.

The results for the individual test-compounds are shown in Tables 23-30. These tables summarize the determined MIC and MBC-values for the tested germs in the last column.

The growth of bacteria is indicated for the duplicate plates by a + (i.e., growth) or a − (i.e., no growth), +− indicates weak growth on both plates or growth on one plate and no growth on the other plate. All bacteria show appropriate growth on the respective control plate not containing any test compound. No influence of the used diluent (Aqua purifacata) was observed. No contamination is observed on the control-plates.

TABLE 23

MIC values for Neramexane-Mesylate at pH 5.5

| | Final Concentration (%) | | | | | | | | | | MIC in (%) |
|---|---|---|---|---|---|---|---|---|---|---|---|
| | 6.25 | 3.13 | 2.50 | 1.56 | 0.63 | 0.31 | 0.16 | 0.08 | 0.04 | 0.01 | |
| *Propionibacterium acnes* | − − | − − | − − | − − | − − | − − | − − | − − | + + | + + | 0.08 |

TABLE 23-continued

MIC values for Neramexane-Mesylate at pH 5.5

| | Final Concentration (%) | | | | | | | | | | MIC in |
|---|---|---|---|---|---|---|---|---|---|---|---|
| | 6.25 | 3.13 | 2.50 | 1.56 | 0.63 | 0.31 | 0.16 | 0.08 | 0.04 | 0.01 | (%) |
| *Propionibacterium avidum* | − − | − − | − − | − − | − − | − − | − − | − − | + + | + + | 0.08 |
| *Propionibacterium granulosum* | − − | − − | − − | − − | − − | − − | − − | − − | + + | + + | 0.08 |
| *Staphylococcus epidermidis* | − − | − − | − − | − − | − − | − − | − − | + + | + + | + + | 0.16 |

TABLE 24

MBC values for Neramexane-Mesylate at pH 5.5

| | Final Concentration (%) | | | | | | | | MBC in |
|---|---|---|---|---|---|---|---|---|---|
| | 6.25 | 3.13 | 2.50 | 1.56 | 0.63 | 0.31 | 0.16 | 0.08 | (%) |
| *Propionibacterium acnes* | − − | − − | − − | − − | + + | + + | + + | + + | 1.56 |
| *Propionibacterium avidum* | − − | − − | − − | − − | − − | + + | + + | + + | 0.63 |
| *Propionibacterium granulosum* | − − | − − | − − | − − | − − | + + | + + | + + | 0.63 |
| *Staphylococcus epidermidis* | − − | − − | − − | − − | + + | + + | + + | not tested | 1.56 |

TABLE 25

MIC values for Neramexane-Mesylate at pH 6.0

| | Final Concentration (%) | | | | | | | | | | MIC in |
|---|---|---|---|---|---|---|---|---|---|---|---|
| | 6.25 | 3.13 | 2.50 | 1.56 | 0.63 | 0.31 | 0.16 | 0.08 | 0.04 | 0.01 | (%) |
| *Propionibacterium acnes* | − − | − − | − − | − − | − − | − − | − − | − − | + + | + + | 0.08 |
| *Propionibacterium granulosum* | − − | − − | − − | − − | − − | − − | − − | − − | + − | + + | 0.08 |

TABLE 26

MBC values for Neramexane-Mesylate at pH 6.0

| | Final Concentration (%) | | | | | | | | MBC in |
|---|---|---|---|---|---|---|---|---|---|
| | 6.25 | 3.13 | 2.50 | 1.56 | 0.63 | 0.31 | 0.16 | 0.08 | (%) |
| *Propionibacterium acnes* | − − | − − | − − | − − | − − | + + | + + | + + | 0.63 |
| *Propionibacterium granulosum* | − − | − − | − − | − − | − − | − − | + + | + + | 0.31 |

TABLE 27

MIC values for Neramexane-Mesylate at pH 7.4

| | Final Concentration (%) | | | | | | | | | | MIC in |
|---|---|---|---|---|---|---|---|---|---|---|---|
| | 6.25 | 3.13 | 2.50 | 1.56 | 0.63 | 0.31 | 0.16 | 0.08 | 0.04 | 0.01 | (%) |
| *Propionibacterium acnes* | − − | − − | − − | − − | − − | − − | − − | + + | + + | + + | 0.16 |
| *Propionibacterium granulosum* | − − | − − | − − | − − | − − | − − | − − | − − | + − | + + | 0.08 |

TABLE 28

MBC values for Neramexane-Mesylate at pH 7.4

| | Final Concentration (%) | | | | | | | | MBC in |
|---|---|---|---|---|---|---|---|---|---|
| | 6.25 | 3.13 | 2.50 | 1.56 | 0.63 | 0.31 | 0.16 | 0.08 | (%) |
| *Propionibacterium acnes* | − − | − − | − − | − − | + + | + + | + + | not tested | 1.56 |
| *Propionibacterium granulosum* | − − | − − | − − | − − | + + | + + | + + | + + | 1.56 |

TABLE 29

MIC values for Neramexane-HCl at pH 5.5

| | Final Concentration (%) | | | | | | | | | | MIC in |
|---|---|---|---|---|---|---|---|---|---|---|---|
| | 1.56 | 0.63 | 0.31 | 0.16 | 0.08 | 0.04 | 0.02 | 0.01 | 0.005 | 0.002 | (%) |
| *Propionibacterium acnes* | − − | − − | − − | − − | + + | + + | + + | + + | + + | + + | 0.16 |
| *Propionibacterium avidum* | − − | − − | − − | − − | + − | + + | + + | + + | + + | + + | 0.16 |
| *Propionibacterium granulosum* | − − | − − | − − | − − | − − | + + | + + | + + | + + | + + | 0.08 |
| *Staphylococcus epidermidis* | − − | − − | + + | + + | + + | + + | + + | + + | + + | + + | 0.63 |

TABLE 30

MBC values for Neramexane-HCl at pH 5.5

| | Final Concentration (%) | | | | | MBC in |
|---|---|---|---|---|---|---|
| | 1.56 | 0.63 | 0.31 | 0.16 | 0.08 | (%) |
| *Propionibacterium acnes* | − − | + + | + + | + + | not tested | 1.56 |
| *Propionibacterium avidum* | − − | + + | + + | + + | not tested | 1.56 |
| *Propionibacterium granulosum* | − − | − − | + + | + + | + + | 0.63 |
| *Staphylococcus epidermidis* | + + | + + | not tested | not tested | not tested | >1.56 |

Results

Table 31 summarizes the MIC and MBC values for all test-compounds as established in this study. In general it has to be considered that values determined by the used method can vary by a factor of 2 (for 1:2 dilutions).

TABLE 31

Summary of determined MIC and MBC values (given in %)

| | P. acnes | | P. avidium | | P. granulosum | | S. epidermidis | |
|---|---|---|---|---|---|---|---|---|
| Compound | MIC | MBC | MIC | MBC | MIC | MBC | MIC | MBC |
| Neramexane-Mesylate pH 5.5 | 0.08 | 1.56 | 0.08 | 0.63 | 0.08 | 0.63 | 0.16 | 1.56 |
| Neramexane-Mesylate pH 6.0 | 0.08 | 0.63 | not tested | not tested | 0.08 | 0.31 | not tested | not tested |
| Neramexane-Mesylate pH 7.4 | 0.16 | 1.56 | not tested | not tested | 0.08 | 1.56 | not tested | not tested |
| Neramexane-HCl pH 5.5 | 0.16 | 1.56 | 0.16 | 1.56 | 0.08 | 0.63 | 0.63 | >1.56 |

Neramexane exhibits antibacterial activity with respect to all acne-relevant bacterias tested. Within the range of this assay the established MIC values and MBC values at the skin relevant pH 5.5 are comparable for the different bacteria-strains. Thus, Neramexane demonstrates similar efficacy against all tested bacterias.

There is also no obvious effect of the pH on this anti-bacterial activity. The MIC- and MBC values established at pH 6.0 and pH 7.4 are within the same range as those established at pH 5.5. The same holds true for the MIC- and MBC-values obtained with Neramexane-HCl. With the exception of values for *S. epidermidis*, these values differ max. by a factor 2 from those obtained with Neramexane-Mesylate. These data demonstrate that the salt-form of the active has minor impact on the anti-bacterial activity of Neramexane.

Thus, the observed anti-bacterial activity towards acne relevant bacterias is a property of Neramexane as such.

Example 6

Anti-Microbial Potency of Neramexane Against Relevant Bacterias—Determination of Bactericidal Activity in a Quantitative Suspension Assay To further assess the anti-microbial potency of Neramexane a quantitative suspension assay is performed.

Procedure 1.0 ml of the bacterial test suspension (microbial count: $1.5\text{-}5.0 \times 10^8$ cfu/ml) and 1.0 ml distilled water is added to 8.0 ml of the product test solution. The stopwatch is started. At the end of the exposure time, 0.1 ml of the test mixture is added to 50 ml rinsing liquid (=test neutralization mixture, TNM, $10^0$). Two dilutions of the TNM are prepared by pipetting 500 µl of TNM to 9.0 ml of tryptone-NaCl (represents a dilution $10^{-2}$ of TNM before filtration) resp. 50 µl of TNM to 9.0 ml of tryptone-NaCl (represents a dilution $10^{-3}$ of TNM before filtration). The TNM (in duplicate) and each of the dilutions are transferred to a membrane filter device fitted with a membrane filter (0.45 µm) and filtered immediately. Subsequently, the filter is washed with 150 ml distilled water. The membranes are transferred to agar plates. After incubation under appropriate conditions, colonies are counted and reported.

Neramexane-mesylate is tested at 4 different concentrations (w/w 0.1%, 0.5%, 2.0%, 5.0%) to assess its bactericidal activity against *Propionibacterium acnes* (ATCC 11828). In addition to the effect of the concentration of Neramexane, the relevance of the contact time with the bacterias is assessed at 4 different incubation times (5 min, 30 min, 6 h, 24 h).

After the desired incubation time, the complete elimination of the test compound from the assay is ensured by membrane filtration. Bacterial suspensions with a microbial count ranging from $1.5\text{-}5.0 \times 10^8$ cfu/ml are used. All assays are performed at the skin relevant pH of 5.5.

The read out is reduction of the bacterial number in the assay, expressed as log-reduction. This reduction of the bacterial count is correlated to the ability of a compound to kill the bacteria, thus, corresponding to its MBC value. A >5-fold log reduction is required for a surface-disinfection compound and a >3-fold log reduction for a hand-disinfection compound.

Results

A summary of the results for Neramexane-mesylate is shown in Table 32.

TABLE 32

Summary of log-reduction values for Neramexane-mesylate

| Concentration | Contact time | | | |
|---|---|---|---|---|
| | 5 min | 30 min | 6 h | 24 h |
| 0.1% | <1.41 | <1.41 | <1.41 | <1.41 |
| 0.5% | <1.41 | <1.41 | 2.60 | >5.48 |
| 2.0% | <1.41 | >5.48 | >5.48 | >5.48 |
| 5.0% | 4.33 | >5.48 | >5.48 | >5.48 |

A concentration of 0.5% efficiently eliminates *P. acnes* in this assay after 24 h contact time. Even after 6 h contact a significant log-reduction (2.6-fold) is obtained. With a 2.0% solution, the maximum reduction within this assay of >5-fold log-reduction is reached after only 30 min incubation. With a 5% solution, a log-reduction of 4.33-fold was obtained after only 5 min incubation.

These data confirm that Neramexane efficiently eliminates the acne relevant *P. acnes* bacteria in suspension. Depending on the concentration, only a short incubation time is necessary to demonstrate this antimicrobial activity.

Example 7

Anti-Microbial Potency of Neramexane Against *Streptococcus pyogenes* and *Staphylococcus aureus*—Determination of MIC Values by the Agar Dilution Method To assess the anti-microbial potency of Neramexane against bacteria strains which are relevant for atopic dermatitis and localized skin infections ("impetigo"), the minimal inhibitory concentration (MIC) against the following bacteria is established:

| | | |
|---|---|---|
| 5. | *Staphylococcus aureus* | ATCC 6538 |
| 6. | *Streptococcus pyogenes* | ATCC 12344 |

While infections with *Staphylococcus aureus* is a very common complication in atopic dermatitis the same bacteria-strain is also involved in localized skin infections ("impetigo") together with *Streptococcus pyogenes*.

Procedure

The MICs of the samples are determined using the agar dilution method based on DIN 58940. Petri dishes of 5.5 cm diameter are poured with 2.5 ml of freshly prepared Mueller-Hinton agar 2-fold concentrated (Merck company, Cat-No 1.05437), pH 5.5, maintained in liquid form at 50° C., to which the sample dilutions at various concentrations has been added at 50.0 vol.-%.

Preparation of Test Solution and Agar Plates

Neramexane-Mesylate is tested in the concentration range of $6.25\text{-}1 \times 10^{-2}\%$. All test solutions are adjusted to pH 5.5.

Execution of the Agar Dilution Test

For inoculation, 1 µl of the respective germ suspension is placed on the centre of each agar plate. After drying, inoculated plates are incubated at 36.0±2.0° C. The basis for the length of incubation period is the respective growth control cultivated in parallel.

TABLE 33

Test Organisms and Microbial Counts of Test Microbe Suspensions

| No | Test Organisms | | CFU*/ml |
|---|---|---|---|
| 1 | *Staphylococcus aureus* | ATCC 6538 | $3.4 \times 10^7$ |
| 2 | *Streptococcus pyogenes* | ATCC 12344 | $3.6 \times 10^7$ |

*= colony forming units

The test microbe suspension is prepared by inoculating a few individual colonies of the respective bacteria into sterile saline solution until a turbidity corresponding to the McFarland standard 1.0 (approximately $10^8$ cfu/ml) is reached. After that, the test microbe suspensions are further diluted 1:10 with saline solution and the microbial counts (see Table 33) are determined by the surface spread method using a spiral plater.

The agar plates are incubated under the conditions given in Table 34 and subsequently evaluated. The MIC-values as given represent the lowest concentration of the active substance at which there is no macroscopically visible growth.

Minimal, barely visible growth or few small individual colonies are evaluated as inhibition.

TABLE 34

Inoculation and Incubation Conditions

| Test Organism No | Growth Conditions | Nutrient Medium | Incubation |
|---|---|---|---|
| ½ | Aerobic | Mueller-Hinton agar | 16-20 h at 36° C. |

Evaluation of Data and Results

The results for the individual test-compounds are shown in Tables 35. The growth of bacteria is indicated for the duplicate plates by a + (i.e., growth) or a − (i.e., no growth), +− indicates weak growth on both plates or growth on one plate and no growth on the other plate. Both bacteria-strains show appropriate growth on the respective control plate not containing any test compound. No influence of the used diluent (Aqua purifacata) is observed. No contamination is observed on the control-plates. In general it has to be considered that values determined by the used method can vary by a factor of 2 (for 1:2 dilutions).

TABLE 35

MIC values for Neramexane-Mesylate at pH 5.5

| | Final Concentration (%) | | | | | | | | | | MIC in |
|---|---|---|---|---|---|---|---|---|---|---|---|
| | 6.25 | 3.13 | 2.50 | 1.56 | 0.63 | 0.31 | 0.16 | 0.08 | 0.04 | 0.01 | (%) |
| Staphylococcus aureus | − − | − − | − − | − − | +− | + + | + + | + + | + + | + + | 1.56 |
| Streptococcus pyogenes | − − | − − | − − | − − | − − | − − | − − | − − | + + | + + | 0.08 |

Neramexane exhibits antibacterial activity with respect to *Staphylococcus aureus* which is relevant for atopic dermatitis and the skin disease impetigo contagiosa and acts even to greater extend against *Streptococcus pyogenes*, which is also involved in impetigo contagiosa.

The used agar dilution assay is a standard assay for establishing the antibacterial potential of a test compound. The growth conditions and inoculated number of bacteria avoid an overestimation of the anti-bacterial effect of a test-compound. The chosen skin relevant pH of 5.5 further promotes the generation of data which are relevant for treatment of skin associated bacterial infections. The obtained data are thus adequate for determination of the therapeutic antibacterial potential of Neramexane against both bacterial strains.

Therefore these data allow predication of the therapeutic use of Neramexane in indications with involvement of the tested bacterial-strains.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference.

We claim:

1. A method of treating inflammatory skin diseases, wherein the inflammatory skin disease is not psoriasis, in a subject in need thereof, comprising administering an effective amount of a 1-amino-alkylcyclohexane derivative selected from neramexane and pharmaceutically acceptable salts thereof.

2. The method according to claim 1, wherein the 1-aminoalkylcyclohexane derivative is neramexane mesylate.

3. The method according to claim 2, wherein neramexane mesylate is administered in a range from about 5 mg to about 150 mg/day.

4. The method according to claim 2, wherein neramexane mesylate is administered in a range from about 5 mg to about 100 mg/day.

5. The method according to claim 2, wherein neramexane mesylate is administered at about 5 mg to about 75 mg/day.

6. The method according to claim 2, wherein neramexane mesylate is administered at about 50 mg/day.

7. The method according to claim 2, wherein neramexane mesylate is administered at about 75 mg/day.

8. The method according to claim 1, wherein the 1-aminoalkylcyclohexane derivative is administered once a day, twice a day (b.i.d.), or three times a day.

9. The method according to claim 1, wherein the 1-aminoalkylcyclohexane derivative is administered in a topical formulation.

10. The method according to claim 9, wherein the 1-aminoalkylcyclohexane derivative is administered between 0.1 and 99% by weight of the formulation.

11. The method according to claim 1, wherein the 1-aminoalkylcyclohexane derivative is administered in an oral formulation.

12. The method according to claim 1, wherein the inflammatory skin disease is selected from acne, rosacea, eczema, atopic dermatitis, and oily skin.

13. The method according to claim 1, wherein the inflammatory skin disease is acne.

14. The method according to claim 1, wherein the inflammatory skin disease is atopic dermatitis.

15. The method according to claim 1, wherein the inflammatory skin disease is impetigo contagiosa.

16. The method according to claim 1, wherein the inflammatory skin disease is not psoriasis.

17. The method according to claim 9, wherein the inflammatory skin disease is selected from acne, rosacea, eczema, atopic dermatitis, and oily skin.

18. A pharmaceutical composition comprising a therapeutically effective amount of a 1-amino-alkylcyclohexane derivative selected from neramexane and pharmaceutically acceptable salts thereof in combination with an additional pharmaceutical agent selected from antimicrobial agents, antibiotics, retinoids, and steroids and, optionally, at least one pharmaceutically acceptable carrier or excipient.

19. The pharmaceutical composition according claim 18, wherein the 1-amino-alkylcyclohexane derivative is neramexane mesylate.

20. The pharmaceutical composition according to claim 18 in the form of a topical formulation.

21. The pharmaceutical composition according to claim 18 in the form of an oral formulation.

* * * * *